US009295543B2

(12) United States Patent
Allen-Hoffmann et al.

(10) Patent No.: US 9,295,543 B2
(45) Date of Patent: Mar. 29, 2016

(54) SKIN SUBSTITUTES WITH IMPROVED PURITY

(75) Inventors: B. Lynn Allen-Hoffmann, Madison, WI (US); Cathy Ann-Rasmussen Ivarie, Marshall, WI (US); John M. Centanni, Madison, WI (US)

(73) Assignee: STRATATECH CORPORATION, Madison, WI (US)

( * ) Notice: Subject to any disclaimer, the term of this patent is extended or adjusted under 35 U.S.C. 154(b) by 309 days.

(21) Appl. No.: 11/375,950

(22) Filed: Mar. 15, 2006

(65) Prior Publication Data

US 2006/0258001 A1    Nov. 16, 2006

Related U.S. Application Data

(60) Provisional application No. 60/662,831, filed on Mar. 17, 2005.

(51) Int. Cl.
*C12N 5/00* (2006.01)
*A61F 2/10* (2006.01)
*C12N 5/071* (2010.01)

(52) U.S. Cl.
CPC .............. *A61F 2/105* (2013.01); *C12N 5/0629* (2013.01); *C12N 5/0698* (2013.01); *C12N 2502/094* (2013.01); *C12N 2502/1323* (2013.01)

(58) Field of Classification Search
CPC .......... A61K 35/36; C12N 5/071; C12N 5/18; C12N 5/22
USPC .......................... 435/243, 325, 371, 354, 357
See application file for complete search history.

(56) References Cited

U.S. PATENT DOCUMENTS

| 7,011,828 | B2 | 3/2006 | Reubinoff |
| 7,462,448 | B2 | 12/2008 | Allen-Hoffmann et al. |
| 2002/0164308 | A1 | 11/2002 | Reubinoff |
| 2002/0164793 | A1* | 11/2002 | Conrad et al. ................. 435/371 |
| 2005/0244962 | A1* | 11/2005 | Thomson et al. ............. 435/366 |

FOREIGN PATENT DOCUMENTS

| WO | 97/23602 | 7/1997 |
| WO | 02/070729 | 9/2002 |
| WO | 02/086510 | 10/2002 |
| WO | 2004/013606 | 2/2004 |
| WO | 2005/012508 | 2/2005 |

OTHER PUBLICATIONS

Nicole Maas-Szabowski, Anja Starker and Norbert E. Fusenig "Epidermal tissue regeneration and stromal interaction in HaCaT cells is initiated by TGF-a" Journal of Cell Science 116, 2937-2948 © 2003.*
Marjorie A. Phillips and Robert H. Rice "Convergent Differentiation in Cultured Rat Cells from Nonkeratinized Epithelia:Keratinocyte Character and Intrinsic Differences" The Journal of Cell Biology • vol. 97 Sep. 1983 686-691.*
B. Lynn Allen-Hoffman et al. "Normal Growth and Differentiation in a Spontaneously Immortalized Near-Diploid Human Keratinocyte Cell Line, NIKS" Journal of Investigative Dermatology vol. 114 No. 3 Mar. 2000 p. 444-455.*
Human Cell Culture, vol. V, Primary Mesenchymal Cells, Edited by Koller, Palsson and Master, published 2001 Kluwer, pp. 116-117.*
Methods in Molecular Biology 5, Animal Cell Culture, Edited by Pollard and Walker, Published 1990 Crescent Manor p. 317-319.*
Hunyadi et al. "Crpopreserved 3T3 Fibroblasts Retain Their Capacity to Enhance the Growth of Human Keratinocyte Cultures" Acre Derm Vencreo, (Stockh) 1989, 69: 509-543.*
Eckert et al. "Molecular Biology of Keratinocyte Differentiation" Environmental Health Perspectives vol. 80, pp. 109-116, 1989.*
Blacker et al. "Mitomycin C-Treated 3T3 Fibroblasts Used as Feeder Layers for Human Keratinocyte Culture Retain the Capacity to Generate Eicosanoids" vol. 89. No. 6, 1987, pp. 536-539.*
Parodi et al. "Species Identification and Confirmation of Human and Animal Cell Lines: A PCR-Based Method" BioTechniques 32:432-440 (Feb. 2002).*
Thomas E. Gray et al. "Quantitation of Cell Proliferation, Colony Formation, and Carcinogen Induced Cytotoxicity of Rat Tracheal Epithelial Cells Grown in Culture on 3T3 Feeder Layers" In Vitro vol. 19, No. 7, Jul. 1983, pp. 559-570.*
Alitalo et al., Extracellular matrix proteins of human epidermal keratinocytes and feeder 3T3 cells. The Journal of Cell Biology. vol. 94 (1982) pp. 497-505.*
Rheinwald and Green, Serial cultivation of human epidermal keratinocytes: the formation of keratinizing colonies from single cells. Cell. vol. 6 (Nov. 1975) pp. 331-344.*
Butcher et al., Mitomycin C-treated 3T3/B (3T3/A31) cell feeder layers in hybridoma technology. Journal of Immunological Methods, vol. 107 (1988) pp. 245-251.*
Invitrogen. Useful numbers for cell culture. Datasheet. Retrieved from the internet on Oct. 17, 2014 from <URL: http://tools.lifetechnologies.com/downloads/Useful_Numbers_Y14472_Useful_Nmbrs.pdf>.*
Andre B.H. Choo "Expansion of Pluripotent Human Embryonic Stem Cells on Human 1-32 Feeders" Biotechnology and Bioengineering 88(3) 2004 y L.PONCmO, L. Duma, B. Oliviero, N. Gibelli, P. Pedrazzoli, G. Robustelli 1-32 Della Cuna "Mitomycin C as an Alternative to Irradiation to Inhibit the Feeder Layer Growth in Long-term Culture Assays" Cytotherapy 2(4) 2000 p. 281.
Cheng, Linzhao, et al., "Human Adult Marrow Cells Support Prolonged Expansion of Human Embryonic Stem Cells in Culture," Stem Cells (Miamisburg), vol. 21, No. 2 (2003), pp. 131-142.
Daniels, J.T., et al., "Human Keratinocyte Isolation and Cell Culture: A Survey of Current Practices in the UK," Burns, vol. 22, No. 1 (1996), pp. 35-39.
Ponchio, L., et al., "Mitomycin C as an Alternative to Irradiation to Inhibit the Feeder Layer Growth in Long-Term Culture Assays", Cytotherapy, vol. 2, No. 4 (2000), p. 281.
Peel and Hamm, "Growth and Differentiation of Human Keratinocytes Without a Feeder Layer or Conditioned Medium," In Vitro (1980), pp. 516-525.

* cited by examiner

*Primary Examiner* — Laura Schuberg
*Assistant Examiner* — Kara Johnson
(74) *Attorney, Agent, or Firm* — Casimir Jones, S.C.

(57) ABSTRACT

The present invention relates to in vitro cultured skin substitutes. In particular, the present invention relates to compositions and methods for the development of cultured skin substitutes using NIKS cells.

12 Claims, 3 Drawing Sheets

SEQUENCE LISTING

```
<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Synthetic

<400> SEQUENCE: 1
gaattcacta tgaaagtcag attagatc                                              28

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
gaattccata accattacag ttggccaacc                                            30

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
gcccggcccc tcttgtcccc                                                       20

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
gagccggggt catccggtg                                                        19
```

SKIN SUBSTITUTES WITH IMPROVED PURITY

This application claims the benefit of U.S. Provisional Patent Application No. 60/662,831 filed Mar. 17, 2005, incorporated by reference in its entirety.

FIELD OF THE INVENTION

The present invention relates to in vitro cultured skin substitutes. In particular, the present invention relates to compositions and methods for the development of cultured skin substitutes.

BACKGROUND

The skin is the largest organ of the human body. The skin consists of the epidermal and dermal layers. The epidermis is the outer layer, sitting on and nourished by the thicker dermis. These two layers are approximately 1-2 mm (0.04-0.08 in) thick. The epidermis consists of an outer layer of dead cells, which provides a tough, protective coating, and several layers of rapidly dividing cells called keratinocytes. The dermis contains the blood vessels, nerves, sweat glands, hair follicles, and oil glands. The dermis consists mainly of connective tissue, primarily the protein collagen, which gives the skin its flexibility and provides structural support. Fibroblasts, which make collagen, are the main cell type in the dermis.

Skin protects the body from fluid loss, aids in temperature regulation, and helps prevent disease-causing bacteria or viruses from entering the body. Skin that is damaged extensively by burns or non-healing wounds can compromise the health and well-being of the patient. More than 50,000 people are hospitalized for burn treatment each year in the United States, and 5,500 die. Approximately 4 million people suffer from non-healing wounds, including 1.5 million with venous ulcers and 800,000 with diabetic ulcers, which result in 55,000 amputations per year in the United States.

The treatment of severely wounded skin is complicated because the dermis is not capable of self-restoration. One procedure for treating wounded skin is skin grafting. Most commonly, skin grafting is used in the reconstruction of skin after the surgical removal of cutaneous malignancies. However, skin grafts are also used to cover chronic nonhealing cutaneous ulcers, to replace tissue lost in full-thickness burns, or to restore hair to areas of alopecia.

Skin for grafting can be obtained from another area of the patient's body, called an autograft, if there is enough undamaged skin available, and if the patient is healthy enough to undergo the additional surgery required. Alternatively, skin autografts can be made with a person's own keratinocytes through a culturing process. The use of cultured keratinocytes requires an initial small skin biopsy specimen, approximately three weeks to grow the keratinocytes in culture, and may require the use of additional products to stabilize the cultured epidermal layer once surgically applied. Such products may be obtained from another person (donor skin from cadavers is frozen, stored, and available for use), called an allograft, or from an animal (usually a pig), called a xenograft. Allografts and xenografts may also be directly applied should autograft material be unavailable, however these products provide only temporary covering—they are rejected by the patient's immune system within 7-10 days and must be replaced with an autograft.

Treatments of severely wounded skin with cultured autografts have shortcomings. In comparison to natural skin, cultured skin is very fragile because it has no dermal layer, and is more susceptible to infection because it has only a few layers of poorly differentiated cells. The use of cultured skin autografts is costly and requires lengthy culture times. Additionally, residual feeder layer cells (e.g., murine-derived feeder layers) used to support the in vitro growth of keratinocytes may constitute an impurity within the growing cells, cell lines, or cell-derived products. As a result, there is a strong need for improved methods and compositions to detect residual feeder layer cells, especially proliferating feeder layer cells, within cultured keratinocytes and keratinocyte-based products to ensure purity.

SUMMARY OF THE INVENTION

The present invention relates to in vitro cultured skin substitutes. In particular, the present invention relates to compositions and methods for the development of cultured skin substitutes.

Accordingly, the present invention provides methods for providing cells harvested from a feeder layer comprising: a) providing product cells, feeder layer cells, and an agent that prevents cellular replication; b) treating the feeder layer cells with the agent that prevents cellular replication; c) assaying the feeder layer cells for replication; d) culturing the product cells on the feeder layer cells; e) separating the product cells and the feeder layer cells; f) assaying the product cells for the presence of feeder layer cell DNA. The present invention is not limited to the use of any particular type of product cell. Indeed, use of a variety of product cells is contemplated. In some embodiments, the product cells are capable of stratifying into squamous epithelia. In some embodiments, the product cells are selected from a group consisting of primary and/or immortalized keratinocytes. In some preferred embodiments, the keratinocytes are near-diploid human keratinocyte (NIKS). The present invention is not limited to the use of any particular feeder layer. Indeed, the use with a variety of feeder layers is contemplated. In some embodiments, the feeder layer provides growth factors and extracellular matrix molecules necessary for keratinocyte cell growth. In some embodiments, the feeder layer is murine fibroblast cells. In some preferred embodiments, the murine fibroblast cells are 3T3 cells. The present invention is not limited to the use of any particular agent that prevents cellular replication. Indeed, the use of a variety of such agents is contemplated. In some preferred embodiments, the agent is mitomycin-C. In some preferred embodiments, separating the product cells and the feeder layer cells is accomplished with EDTA. In some embodiments, assaying the feeder layer cells for replication is accomplished with a proliferation assay. In some preferred embodiments, the feeder layer cells are substantially free of replicating mouse cells. In other preferred embodiments, the feeder layer cells demonstrating cell replication are discarded. In still other preferred embodiments, assaying the product cells for the presence of feeder layer cell DNA is accomplished with a mouse DNA PCR assay. In some embodiments, the product cells harvested from a feeder layer containing greater than $1.0 \times 10^4$ feeder layer cell DNA equivalents are discarded. In other embodiments, the product cells harvested from a feeder layer contain less than about 0.015% feeder cell DNA equivalents within the total cell population. In some embodiments, the product cells are stem cells. In some embodiments, the product cells are selected from group consisting of mammalian cells. In further embodiments, the feeder layer cells demonstrating cell replication are discarded. In some embodiments, the methods further comprise incorporating the product cells in a skin equivalent. In some preferred embodiments, the skin equivalent is substantially free of residual feeder layer cells.

In some embodiments, the methods further comprise the step of incorporating the product cells into a product. In some preferred embodiments, the product is substantially free of residual feeder layer cells. In some embodiments, the present invention provides cells produced according to the methods described above.

In some embodiments, the present invention provides a skin equivalent composition comprising stratified keratinocyte cells derived from in vitro culture with a feeder layer, wherein the skin equivalent is substantially free of residual feeder layer cells. The present invention is not limited to any particular source of keratinocytes. Indeed, the use of a variety of sources of keratinocytes is contemplated. In some preferred embodiments, the keratinocyte cells are NIKS cells. The present invention is not limited to the use of any particular feeder layer. Indeed, the use with a variety of feeder layers is contemplated. In some embodiments, the feeder layer provides growth factors and extracellular matrix molecules necessary for keratinocyte cell growth. In some embodiments, the feeder layer is murine fibroblast cells. In some preferred embodiments, the murine fibroblast cells are 3T3 cells. The present invention is not limited to the use of any particular agent that prevents cellular replication. Indeed, the use of a variety of such agents is contemplated. In some preferred embodiments, the agent is mitomycin-C. In some embodiments, the skin equivalent is separated from the feeder layer with EDTA. In further embodiments, the feeder layer is substantially free of replicating feeder cells. In some preferred embodiments, the skin equivalents contain less than 0.015% feeder cell DNA equivalents within the total cell population.

DEFINITIONS

Figure 1:
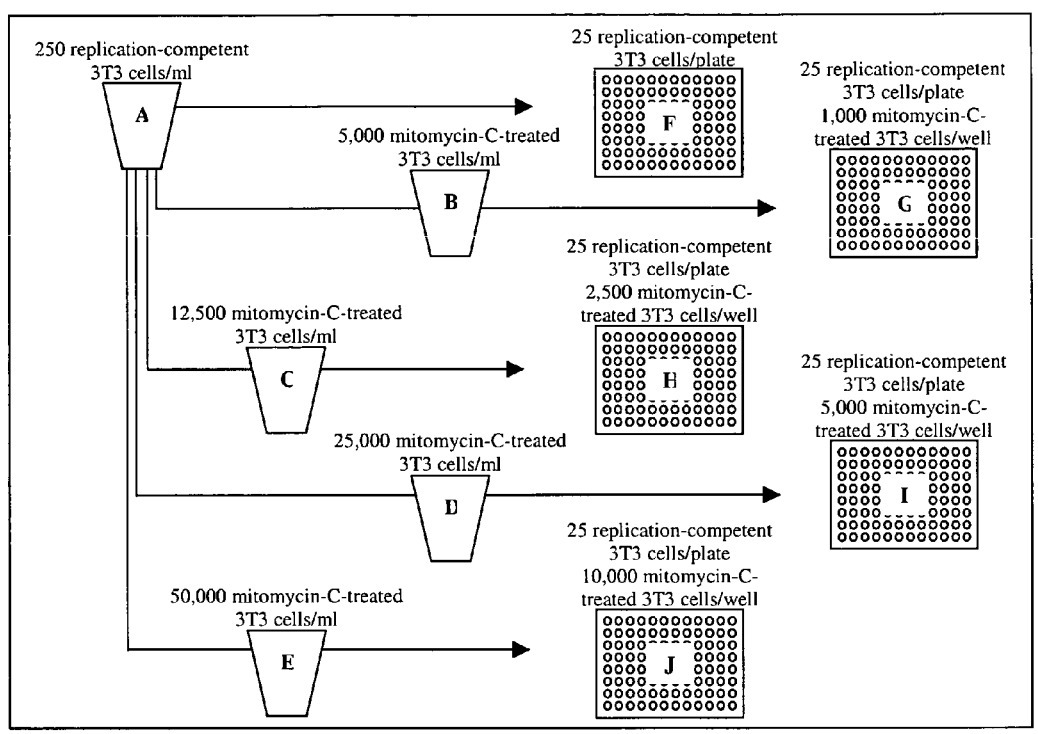
FIG. 1 depicts cellular preparation, dilution, and plating scheme for cell density investigation. Steps 1 and 2 involve the dilution of cells, and steps 3-7 involve the combination and plating of cells. In step 1, proliferating, replication-competent 3T3 fibroblasts were harvested, counted, and diluted in 50 ml 3T3 culture medium to a cell density of 250 cells/ml [A]. In step 2, cryopreserved mitomycin-C-treated 3T3 cells were thawed, counted, and diluted in 3T3 culture medium to cell densities of 5,000 cells/ml [B], 12,500 cells/ml [C], 25,000 cells/ml [D], and 50,000 cells/ml [E]. In step 3, 573 µl of replication-competent 3T3 cell suspension [A] was added to 110 ml of 3T3 culture medium. 200 µl of the replication-competent 3T3 cell suspension was transferred to each well resulting in 25 replication-competent 3T3 cells per plate [F]. In step 4, 573 µl of replication-competent 3T3 cell suspension [A] was added to 110 ml of mitomycin-C-treated 3T3 cell suspension [B]. 200 µl of the combined cell suspension was transferred to each well resulting in 1,000 mitomycin-C-treated 3T3 cells per well and 25 replication-competent 3T3 cells per plate [G]. In step 5, 573 µl of replication-competent 3T3 cell suspension [A] was added to 110 ml of mitomycin-C-treated 3T3 cell suspension [C]. 200 µl of the combined cell suspension was transferred to each well resulting in 2,500 mitomycin-C-treated 3T3 cells per well and 25 replication-competent 3T3 cells per plate [H]. In step 6, 573 µl of replication-competent 3T3 cell suspension [A] was added to 110 ml of mitomycin-C-treated 3T3 cell suspension [D]. 200 µl of the combined cell suspension was transferred to each well resulting in 5,000 mitomycin-C-treated 3T3 cells per well and 25 replication-competent 3T3 cells per plate [I]. In step 7, 573 µl of replication-competent 3T3 cell suspension [A] was added to 110 ml of mitomycin-C-treated 3T3 cell suspension [E]. 200 µl of the combined cell suspension was transferred to each well resulting in 10,000 mitomycin-C-treated 3T3 cells per well and 25 replication-competent 3T3 cells per plate [J].

As used herein, the terms "skin equivalent" and "skin substitute" are used interchangeably to refer to an in vitro-derived culture of keratinocytes that has stratified into squamous epithelia in what is termed an organotypic culture.

As used herein, the terms "product cell", "cell product", or "cell-derived product" refers to cells or cell lines capable of in vitro growth on a feeder layer and products generated from cells capable of in vitro growth on a feeder layer. Examples include, but are not limited to, keratinocytes, stem cells, and synthetic cells.

As used herein, the term "feeder layer" refers to a replication-inactivated, cellular-derived substrate used to support in vitro growth of cells or cell lines. Examples of feeder layers include, but are not limited to, 3T3 feeder layers, murine feeder layers, synthetic feeder layers, and synthetic substrates.

As used herein, the term "feeder layer cells" refer to the cells used to produce the feeder layers which support in vitro growth of cells or cell lines. Examples of feeder layer cells include, but are not limited to, 3T3 fibroblasts, murine fibroblasts, and synthetic fibroblasts.

As used herein, the terms "medium" or "growth medium" refer to a liquid medium used to support in vitro growth of cells or cell lines. Examples of growth medium include, but are not limited to, DME medium, supplemented medium, and synthetic growth mediums.

As used herein, the term "dermal equivalent" is used to refer to an in vitro-derived culture comprising collagen and fibroblast cells. It is contemplated that "dermal equivalents" can serve as substrates for differentiation of keratinocytes in an organotypic culture.

As used herein, the term "stem cells" refers to cells competent to undergo more than one developmental fate.

As used herein, the term "growth factor" refers to extracellular molecules that bind to a cell-surface triggering an intracellular signaling pathway leading to proliferation, differentiation, or other cellular response. Examples of growth factors include, but are not limited to, growth factor I, trophic factor, $Ca^{2+}$, insulin, hormones, synthetic molecules, pharmaceutical agents, and LDL.

As used herein, the term "air interface" refers to the interface between the atmosphere and liquid medium in a culture dish.

As used herein, the term "substantially adhered to a sidewall," when used in reference to a dermal equivalent, refers to the physical adherence of a dermal equivalent to a substantially vertical wall, as opposed to the dermal equivalent contracting or pulling away from the substantially vertical wall.

As used herein, the term "organotypic" culture refers to a three-dimensional tissue culture where cultured cells are used to reconstruct a tissue or organ in vitro.

As used herein, the term "near-diploid human keratinocyte cells" or "NIKS cells" refers to cells having the characteristics of the cells deposited as cell line ATCC CRL-12191.

The term "gene" refers to a nucleic acid (e.g., DNA) sequence that comprises coding sequences necessary for the production of a polypeptide or precursor (e.g., GKLF). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "recombinant DNA molecule" as used herein refers to a DNA molecule that is comprised of segments of DNA joined together by means of molecular biological techniques.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets that specify stop codons (i.e., TAA, TAG, TGA).

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response", when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

DETAILED DESCRIPTION

The present invention relates to in vitro cultured skin substitutes. In particular, the present invention relates to compositions and methods for the development of cultured skin substitutes.

Human skin is composed of a dermal layer containing fibroblasts embedded in an extracellular protein matrix and an epidermal layer, consisting primarily of keratinocytes that differentiate to form the outermost, impermeable skin layer. The primary function of human skin is to provide a physical barrier to prevent excessive loss of bodily fluid due to evaporation and to protect the body from environmental insults such as chemicals and microorganisms. This barrier function is localized in the stratum corneum of the skin. Defects in skin barrier function have detrimental effects leading to entry of poisonous substances, infection or severe water loss.

Stratified squamous epithelia, such as skin and oral epithelia, are multilayered renewal tissues composed primarily of keratinocytes. Differentiated keratinocytes are continuously lost from the surface and replaced by the proliferation of basal keratinocytes. The rate at which a basal call initiates and completes its differentiation program appears to be tightly regulated, although the molecular controls for such regulation are ill-defined (Fuchs, J. Cell. Sci. Suppl., 17: 197-208 (1993)). In vivo, the final stages of the terminal differentiation process are characterized by numerous changes including filaggrin-mediated keratin intermediate filament bundling, and release of lipids from membrane-coating granules into the intercellular space (Schurer et al., Dermatologica, 183: 77-94 (1991)). The cornified envelope, another terminal differentiation structure consisting of several proteins that are covalently crosslinked by the action of calcium-dependent transglutaminases, is also formed in differentiating keratinocytes (Aeschlimann et al., Thrombosis & Haemostasis, 71(4): 402-15 (1994); Reichert et al., *The cornified envelope: a key structure of terminally differentiating keratinocytes, in Molecular Biology of the Skin*, M. Darmon, Editor. 1993, Academic Press, Inc.: San Diego. 107-150 (1993)). In the epidermis, keratinocytes lose intracellular organelles and enucleate in the upper layers of the tissue, forming a "dead shell" with high tensile strength. Molecular mechanisms which govern keratinocyte enucleation and terminal differentiation are poorly understood. Studies ((Sachsenmeier et al., J. Biol. Chem., 271: 5-8 (1996); Hines et al., Promega Notes, 59: p. 30-36 (1996); Hines et al., J. Biol. Chem., 271(11): 6245-6251 (1996); Polakowska et al., Developmental Dynamics, 199(3): 176-88 (1994); Haake et al., J. Invest. Derm. Symp. Proc., 3: 28-35 (1998)) suggest that terminal differentiation in keratinocytes may constitute a special form of apoptotic cell death.

The present invention provides skin substitutes, and compositions and methods for making skin substitutes. In addition, the present invention provides methods for making skin substitutes without residual murine DNA or murine cells capable of replication. For convenience, the description of the invention is presented in the following sections: A) Sources of Keratinocytes and Other Cells for Creating Skin Substitutes; B) Culture Conditions for Creating Skin Substitutes; and C)

Uses of Skin Substitutes, and D) Use of Methods for Production of Other Cell Products that are Substantially Free of Feeder Layer Cells.

A. Sources of Keratinocytes and other Cells for Creating Skin Substitutes

It is contemplated that the methods of the present invention can be used to create skin substitutes. Generally, any source of cells or cell line that can stratify into squamous epithelia are useful in the present invention. Accordingly, the present invention is not limited to the use of any particular source of cells that are capable of differentiating into squamous epithelia. Indeed, the present invention contemplates the use of a variety of cell lines and sources that can differentiate into squamous epithelia, including both primary and immortalized keratinocytes. Sources of cells include keratinocytes and dermal fibroblasts biopsied from humans and cavaderic donors (Auger et al., In Vitro Cell. Dev. Biol.—Animal 36:96-103; U.S. Pat. Nos. 5,968,546 and 5,693,332, each of which is incorporated herein by reference), neonatal foreskins (Asbill et al., Pharm. Research 17(9): 1092-97 (2000); Meana et al., Burns 24:621-30 (1998); U.S. Pat. Nos. 4,485,096; 6,039,760; and 5,536,656, each of which is incorporated herein by reference), and immortalized keratinocytes cell lines such as NM1 cells (Baden, In Vitro Cell. Dev. Biol. 23(3):205-213 (1987)), HaCaT cells (Boucamp et al., J. cell. Boil. 106:761-771 (1988)); and NIKS cells (Cell line BC-1-Ep/SL; U.S. Pat. No. 5,989,837, incorporated herein by reference; ATCC CRL-12191). Each of these cell lines can be cultured as described below in order to produce a skin equivalent.

In particularly preferred embodiments, NIKS cells are utilized. The discovery of a novel human keratinocyte cell line (near-diploid immortalized keratinocytes or NIKS) provides an opportunity to genetically engineer human keratinocytes for new in vitro testing methods. A unique advantage of the NIKS cells is that they are a consistent source of genetically-uniform, pathogen-free human keratinocytes. For this reason, they are useful for the application of genetic engineering and genomic gene expression approaches to provide skin equivalent cultures with properties more similar to human skin. Such systems will provide an important alternative to the use of animals for testing compounds and formulations. The NIKS keratinocyte cell line, identified and characterized at the University of Wisconsin, is nontumorigenic, exhibits a stable karyotype, and exhibits normal differentiation both in monolayer and organotypic culture. NIKS cells form fully stratified skin equivalents in culture. These cultures are indistinguishable by all criteria tested thus far from organotypic cultures formed from primary human keratinocytes. Unlike primary cells however, the immortalized NIKS cells will continue to proliferate in monolayer culture indefinitely. This provides an opportunity to genetically manipulate the cells and isolate new clones of cells with new useful properties (Allen-Hoffmann et al., J. Invest. Dermatol., 114(3): 444-455 (2000)).

The NIKS cells arose from the BC-1-Ep strain of human neonatal foreskin keratinocytes isolated from an apparently normal male infant. In early passages, the BC-1-Ep cells exhibited no morphological or growth characteristics that were atypical for cultured normal human keratinocytes. Cultivated BC-1-Ep cells exhibited stratification as well as features of programmed cell death. To determine replicative lifespan, the BC-1-Ep cells were serially cultivated to senescence in standard keratinocyte growth medium at a density of $3 \times 10^5$ cells per 100-mm dish and passaged at weekly intervals (approximately a 1:25 split). By passage 15, most keratinocytes in the population appeared senescent as judged by the presence of numerous abortive colonies which exhibited large, flat cells. However, at passage 16, keratinocytes exhibiting a small cell size were evident. By passage 17, only the small-sized keratinocytes were present in the culture and no large, senescent keratinocytes were evident. The resulting population of small keratinocytes that survived this putative crisis period appeared morphologically uniform and produced colonies of keratinocytes exhibiting typical keratinocyte characteristics including cell-cell adhesion and apparent squame production. The keratinocytes that survived senescence were serially cultivated at a density of $3 \times 10^5$ cells per 100-mm dish. Typically the cultures reached a cell density of approximately $8 \times 10^6$ cells within 7 days. This stable rate of cell growth was maintained through at least 59 passages, demonstrating that the cells had achieved immortality. The keratinocytes that emerged from the original senescencing population were originally designated BC-1-Ep/Spontaneous Line and are now termed NIKS. The NIKS cell line has been screened for the presence of proviral DNA sequences for HIV-1, HIV-2, EBV, CMV, HTLV-1, HTLV-2, HBV, HCV, B-19 parvovirus, HPV-16 and HPV-31 using either PCR or Southern analysis. None of these viruses were detected.

Chromosomal analysis was performed on the parental BC-1-Ep cells at passage 3 and NIKS cells at passages 31 and 54. The parental BC-1-Ep cells have a normal chromosomal complement of 46, XY. At passage 31, all NIKS cells contained 47 chromosomes with an extra isochromosome of the long arm of chromosome 8. No other gross chromosomal abnormalities or marker chromosomes were detected. At passage 54, all cells contained the isochromosome 8.

The DNA fingerprints for the NIKS cell line and the BC-1-Ep keratinocytes are identical at all twelve loci analyzed demonstrating that the NIKS cells arose from the parental BC-1-Ep population. The odds of the NIKS cell line having the parental BC-1-Ep DNA fingerprint by random chance is $4 \times 10^{-16}$. The DNA fingerprints from three different sources of human keratinocytes, ED-1-Ep, SCC4 and SCC13y are different from the BC-1-Ep pattern. This data also shows that keratinocytes isolated from other humans, ED-1-Ep, SCC4, and SCC13y, are unrelated to the BC-1-Ep cells or each other. The NIKS DNA fingerprint data provides an unequivocal way to identify the NIKS cell line.

Loss of p53 function is associated with an enhanced proliferative potential and increased frequency of immortality in cultured cells. The sequence of p53 in the NIKS cells is identical to published p53 sequences (GenBank accession number: M14695). In humans, p53 exists in two predominant polymorphic forms distinguished by the amino acid at codon 72. Both alleles of p53 in the NIKS cells are wild-type and have the sequence CGC at codon 72, which codes for an arginine. The other common form of p53 has a proline at this position. The entire sequence of p53 in the NIKS cells is identical to the BC-1-Ep progenitor cells. Rb was also found to be wild-type in NIKS cells.

Anchorage-independent growth is highly correlated to tumorigenicity in vivo. For this reason, the anchorage-independent growth characteristics of NIKS cells in agar or methylcellulose-containing medium were investigated. After 4 weeks in either agar- or methylcellulose-containing medium, NIKS cells remained as single cells. The assays were continued for a total of 8 weeks to detect slow growing variants of the NIKS cells. None were observed.

To determine the tumorigenicity of the parental BC-1-Ep keratinocytes and the immortal NIKS keratinocyte cell line, cells were injected into the flanks of athymic nude mice. The human squamous cell carcinoma cell line, SCC4, was used as a positive control for tumor production in these animals. The injection of samples was designed such that animals received SCC4 cells in one flank and either the parental BC-1-Ep keratinocytes or the NIKS cells in the opposite flank. This injection strategy eliminated animal to animal variation in tumor production and confirmed that the mice would support vigorous growth of tumorigenic cells. Neither the parental BC-1-Ep keratinocytes (passage 6) nor the NIKS keratinocytes (passage 35) produced tumors in athymic nude mice.

NIKS cells were analyzed for the ability to undergo differentiation in both surface culture and organotypic culture. For cells in surface culture, a marker of squamous differentiation, the formation cornified envelopes was monitored. In cultured human keratinocytes, early stages of cornified envelope assembly result in the formation of an immature structure composed of involucrin, cystatin-α and other proteins, which represent the innermost third of the mature cornified envelope. Less than 2% of the keratinocytes from the adherent BC-1-Ep cells or the NIKS cell line produce cornified envelopes. This finding is consistent with previous studies demonstrating that actively growing, subconfluent keratinocytes produce less than 5% cornified envelopes. To determine whether the NIKS cell line is capable of producing cornified envelopes when induced to differentiate, the cells were removed from surface culture and suspended for 24 hours in medium made semi-solid with methylcellulose. Many aspects of terminal differentiation, including differential expression of keratins and cornified envelope formation can be triggered in vitro by loss of keratinocyte cell-cell and cell-substratum adhesion. The NIKS keratinocytes produced as many as and usually more cornified envelopes than the parental keratinocytes. These findings demonstrate that the NIKS keratinocytes are not defective in their ability to initiate the formation of this cell type-specific differentiation structure.

To confirm that the NIKS keratinocytes can undergo squamous differentiation, the cells were cultivated in organotypic culture. Keratinocyte cultures grown on plastic substrata and submerged in medium replicate but exhibit limited differentiation. Specifically, human keratinocytes become confluent and undergo limited stratification producing a sheet consisting of 3 or more layers of keratinocytes. By light and electron microscopy there are striking differences between the architecture of the multilayered sheets formed in tissue culture and intact human skin. In contrast, organotypic culturing techniques allow for keratinocyte growth and differentiation under in vivo-like conditions. Specifically, the cells adhere to a physiological substratum consisting of dermal fibroblasts embedded within a fibrillar collagen base. The organotypic culture is maintained at the air-medium interface. In this way, cells in the upper sheets are air-exposed while the proliferating basal cells remain closest to the gradient of nutrients provided by diffusion through the collagen gel. Under these conditions, correct tissue architecture is formed. Several characteristics of a normal differentiating epidermis are evident. In both the parental cells and the NIKS cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the parental cells and the NIKS cells. The appearance of flattened squamous cells is evident in the upper layers of keratinocytes and demonstrates that stratification has occurred in the organotypic cultures. In the uppermost part of the organotypic cultures the enucleated squames peel off the top of the culture. To date, no histological differences in differentiation at the light microscope level between the parental keratinocytes and the NIKS keratinocyte cell line grown in organotypic culture have been observed To observe more detailed characteristics of the parental (passage 5) and NIKS (passage 38) organotypic cultures and to confirm the histological observations, samples were analyzed using electron microscopy. Parental cells and the immortalized human keratinocyte cell line, NIKS, were harvested after 15 days in organotypic culture and sectioned perpendicular to the basal layer to show the extent of stratification. Both the parental cells and the NIKS cell line undergo extensive stratification in organotypic culture and form structures that are characteristic of normal human epidermis. Abundant desmosomes are formed in organotypic cultures of parental cells and the NIKS cell line. The formation of a basal lamina and associated hemidesmosomes in the basal keratinocyte layers of both the parental cells and the cell line was also noted. Hemidesmosomes are specialized structures that increase adhesion of the keratinocytes to the basal lamina and help maintain the integrity and strength of the tissue. The presence of these structures was especially evident in areas where the parental cells or the NIKS cells had attached directly to the porous support. These findings are consistent with earlier ultrastructural findings using human foreskin keratinocytes cultured on a fibroblast-containing porous support. Analysis at both the light and electron microscopic levels demonstrate that the NIKS cell line in organotypic culture can stratify, differentiate, and form structures such as desmosomes, basal lamina, and hemidesmosomes found in normal human epidermis.

B. Culture Conditions for Creating Skin Equivalents That Are Substantially Free of Feeder Layer Cells The present invention provides skin equivalents that are substantially free of residual feeder layer cells. By "substantially free" it is meant that the skin equivalents preferably comprise less that 0.001% feeder layer cells on a product cell/feeder layer cell basis. More preferably, skin equivalents will comprise less than 0.0001% feeder layer cells on a product cell/feeder layer cell basis. Feeder layer cells are used to support the in vitro growth of a variety of cells or cell lines including keratinocytes and stem cells. In order to culture some cells, particularly at low or clonal density, it is necessary to use a layer of less fastidious cells to condition the medium. Often the cells of the feeder layer are irradiated or otherwise treated so that they will not proliferate. In some cases the feeder layer may be producing growth factors or cytokines. Feeder layers are often derived from murine fibroblasts. A major drawback with murine feeder layers is the impurity associated with residual murine DNA and/or murine cell replication within the growing cells or cell lines. As a result, there is a strong need for methods aimed at preventing such murine feeder layer impurities.

The present invention provides methods aimed at avoiding murine feeder layer impurities. In particular, the present invention provides methods for generating skin substitutes grown on murine feeder layers that do not contain proliferating feeder layer cells. In some embodiments, the present invention utilizes murine feeder layers. In further embodiments, the present invention utilizes murine 3T3 feeder layers. In even further embodiments, the present invention utilizes 3T3 feeder layers.

Murine 3T3 fibroblasts treated with mitomycin-C to inhibit proliferation, have been used as feeder layers in the cultivation of human keratinocytes in vitro (Watt, F. (1998) In: Cell Biology: A Laboratory Handbook. Vol. 1, 2$^{nd}$ Ed. Academic Press). In addition, feeder layers comprised of mitotically-inactivated 3T3 cells secrete growth factors and extracellular matrix molecules that enhance growth of epithelial cells. In some embodiments of the present invention, the feeder layers will be treated to prevent cell replication. The present invention is not limited to any certain kind of agent to prevent cell replication. In preferred embodiments, the present invention utilizes mitomycin-C.

It is contemplated that in certain embodiments, the production of the present invention involves a multi-step culturing process. However, the present invention is not limited to any particular multi-step culturing process. In preferred embodiments, the multi-step culturing process entails an initiation stage, an expansion stage, and a stratification stage. In some embodiments, these stages are generally referred to as a submerged culture phase.

During the initiation stage, NIKS cells are plated onto replication-inactivated murine 3T3 fibroblasts. In some embodiments, the NIKS cells and murine 3T3 fibroblasts are cryopreserved prior to initiation stage culturing. In some embodiments, between $1 \times 10^6$ and $15 \times 10^6$ replication-inactivated 3T3 cells are utilized. In other embodiments, between $5 \times 10^6$ and $10 \times 10^6$ replication-inactivated 3T3 cells are utilized. Finally, in preferred embodiments, between $7 \times 10^6$ and $8 \times 10^6$ replication-inactivated 3T3 cells (approximately 27,300 cells/cm$^2$ on 275 cm$^2$ plate) are utilized. In some preferred embodiments, the cells are passaged in 50 ml of medium and then treated with 120 ml of mitomycin-C containing medium for 4 hours.

In some embodiments, the amount of time permitted for initiation stage NIKS cell growth is more than one week. In preferred embodiments, the amount of time permitted for NIKS cell growth one week or less. In addition, after initiation stage NIKS cell growth on the feeder layer, the feeder layer is removed. In some embodiments, the feeder layer is removed after less than a monolayer of initiation stage NIKS cell growth. In preferred embodiments, the feeder layer is removed after a monolayer of initiation stage NIKS cell growth is present.

Ethylene diamine tetra acetate (EDTA) treatment selectively removes feeder layers from keratinocyte co-culture thereby eliminating unwanted mitomycin-C-treated replication inactivated 3T3 cells upon completion of a given monolayer culturing phase of NIKS cells. The present invention is not limited to a certain initiation stage feeder layer removal agent. In preferred embodiments, EDTA is used as the initiation stage feeder layer removal agent.

During the expansion stage, NIKS cells grown during the initiation stage are plated onto replication-inactivated murine 3T3 fibroblasts. In preferred embodiments, the NIKS cells utilized are generated in an initiation stage. In some expansion stage embodiments, between $15 \times 10^6$ and $40 \times 10^6$ replication-inactivated 3T3 cells are utilized. In other embodiments, between $20 \times 10^6$ and $25 \times 10^6$ replication-inactivated 3T3 cells are utilized. Finally, in preferred embodiments, between $24 \times 10^6$ and $26 \times 10^6$ replication-inactivated 3T3 cells (approximately 22,700 cells/cm$^2$ on 1125 cm$^2$ plate) are utilized.

In some embodiments the amount of time permitted for NIKS cell growth is more than one week. In preferred embodiments, the amount of time permitted for NIKS cell growth is one week or less. In addition, after NIKS cell growth on the feeder layer, the feeder layer is removed. In some embodiments, the feeder layer is removed after less than a monolayer of expansion stage NIKS cell growth. In preferred embodiments, the feeder layer is removed after a monolayer of expansion stage NIKS cell growth is present. The present invention is not limited to a certain expansion stage feeder layer removal agent. In preferred embodiments, EDTA is used as the expansion stage feeder layer removal agent.

During the stratification stage, NIKS cells are plated onto dermal equivalents. In preferred embodiments, the NIKS cells are generated in an expansion stage. The present invention is not limited to a certain type of dermal equivalent. In preferred embodiments, the dermal equivalent is subject tissue (e.g., horse, human, cat, dog, etc.). In other embodiments, the dermal equivalent may be synthetic tissue. In addition, in some embodiments the amount of time permitted for stratification stage growth is less than two weeks. In preferred embodiments, the amount of time permitted for stratification stage NIKS cell growth is at least two weeks.

The present invention contemplates that a small number of mitomycin-C-treated replication inactivated 3T3 cells may remain following EDTA treatment. As such, in some embodiments, the NIKS cells are assayed to determine the amount of murine DNA present in NIKS cell growth. NIKS cell preparations having more than an acceptable amount of mouse DNA are not used for either stratification or for further processing if stratification has already occurred. The mouse DNA assay may be employed at the conclusion of the initiation stage, expansion stage, and/or the stratification stage. In preferred embodiments, the mouse DNA assay is employed at the conclusion of the initiation, expansion, and stratification stages (i.e., at the conclusion of the submersion stage). In some embodiments, an acceptable amount of murine DNA present in a finished NIKS cell product is less than $5 \times 10^4$ murine cell DNA equivalents/NIKS cell dose. A murine cell DNA equivalent is the amount of mouse cell-specific DNA per haploid chromosome set. A NIKS cell dose is a 44.2 cm$^2$ sample of finished NIKS cell product. In preferred embodiments, an acceptable amount of murine DNA present in a finished NIKS cell product is less than $1.45 \times 10^4$ murine cell DNA equivalents per NIKS cell dose. In addition, murine cells may constitute no more than 0.015% of the total cell population. Table 1 summarizes various calculations of acceptable 3T3 cell limits.

TABLE 1

Calculation of Acceptable 3T3 Cell Limits. Values represent calculations for the lot release test method "Assessment of StrataGraft ™ for Mouse DNA" limit in addition to the historical levels of mouse DNA detected and the theoretical detection of no more than 1 cell DNA equivalent.

|  | Test Method Limit | Historical | Theoretical |
| --- | --- | --- | --- |
| Assessment of StrataGraft ™ for Mouse DNA | No more than 13.2 cell DNA equivalents/0.5 µg DNA | No more than 3.3 cell DNA equivalents/0.5 µg DNA | No more than 1 cell DNA equivalent/0.5 µg DNA |

TABLE 1-continued

Calculation of Acceptable 3T3 Cell Limits. Values represent calculations for the lot release test method "Assessment of StrataGraft ™ for Mouse DNA" limit in addition to the historical levels of mouse DNA detected and the theoretical detection of no more than 1 cell DNA equivalent.

| | Test Method Limit | Historical | Theoretical |
|---|---|---|---|
| Mouse Cell Equivalents per Total Cell Population | 0.015% | 0.004% | 0.0011% |
| Per 8 mm Tissue Punch (0.5 cm$^2$) | No more than 163 cell DNA equivalents/6.2 μg DNA | No more than 41 cell DNA equivalents/6.2 μg DNA | No more than 12.4 cell DNA equivalents/6.2 μg DNA |
| Per StrataGraft ™ Tissue (1 Dose) (44.2 cm$^2$) | No more than $1.45 \times 10^4$ cell DNA equivalents/dose | No more than $3.6 \times 10^3$ cell DNA equivalents/dose | No more than $1.1 \times 10^3$ cell DNA equivalents/dose |
| Per StrataGraft ™ Batch of 5 Tissues (221 cm$^2$) | No more than $7.2 \times 10^4$ cell DNA equivalents/batch | No more than $1.8 \times 10^4$ cell DNA equivalents/batch | No more than $5.5 \times 10^3$ cell DNA equivalents/batch |

An alternative screen may be employed by the present invention to detect feeder layer cells that are capable of replication. Indeed, one goal of the current invention is to provide assurances that each allowable 3T3 cell in a final batch is replication-inactivated and not capable of proliferation. To ensure that the ability of 3T3 fibroblasts to replicate has been completely eliminated by mitomycin-C treatment, each batch of mitomycin-C-treated 3T3 cells may be evaluated by a proliferation assay. The test method examines mitomycin-C-treated 3T3 cells for any evidence of 3T3 proliferation. In preferred embodiments, the standard required for mitomycin-C-treated 3T3 cells to be deemed appropriate for use in the production of the present invention is zero 3T3 proliferation. In some embodiments, the proliferation detection method is used to screen any feeder layer. In other embodiments, the proliferation detection method is used to screen 3T3 feeder layers prior to use in the initiation stage and/or expansion stage. In preferred embodiments, the proliferation detection method is used to screen 3T3 feeder layers prior to use in both the initiation stage and expansion stage.

The proliferation assay and the mouse DNA assay test methods are incorporated at different points in the production process and complement each other. In combination, these two test methods evaluate and effectively eliminate the potential presence of replication-competent 3T3 cells in the final skin substitute product. The mouse DNA assay limits the total amount of 3T3 DNA, expressed as cell DNA equivalents, allowable in the final skin substitute tissue, while the proliferation assay ensures that any intact 3T3 cells present are not capable of replication and subsequent proliferation. Impurities associated with feeder layer usage during cell culture and the production of cultured cell products are a major problem in the art. Product cells, such as keratinocytes or stem cells, grown on feeder layers screened with the mouse DNA assay and the proliferation assay are substantially free of residual feeder layer cells and any resulting impurities. In preferred embodiments, the mouse DNA assay and the proliferation assay are utilized in the production of the present invention.

C. Uses of Skin Substitutes

It is contemplated that the skin substitutes of the present invention have a variety of uses. These uses include, but are not limited to, use for screening compounds (e.g., irritants), substrates for culturing tumors and pathological agents (e.g., human papilloma virus), and use for wound closure and burn treatment. These uses are described in more detail below.

1. Use for Screening Compounds

The skin equivalents of the present invention may be used for a variety of in vitro tests. In particular, the skin equivalents find use in the evaluation of: skin care products, drug metabolism, cellular responses to test compounds, wound healing, phototoxicity, dermal irritation, dermal inflammation, skin corrosivity, and cell damage. The skin equivalents are provided in a variety of formats for testing, including but not limited to, 6-well, 24-well, and 96-well plates. Additionally, the skin equivalents can be divided by standard dissection techniques and then tested. The skin equivalents of the present invention have both an epidermal layer with a differentiated stratum corneum and dermal layer that includes dermal fibroblasts. As described above, in particularly preferred embodiments, the epidermal layer is derived from immortalized NIKS cells. Other preferred cell lines, including NIKS cells, are characterized by i) being immortalized; ii) being nontumorigenic; iii) forming cornified envelopes when induced to differentiate; iv) undergoing normal squamous differentiation in organotypic culture; and v) maintaining cell type-specific growth requirements in submerged culture, wherein said cell type-specific growth requirements include 1) exhibition of morphological characteristics of normal human keratinocytes when cultured in standard keratinocyte growth medium in the presence of mitomycin-C-treated 3T3 feeder cells; 2) dependence on epidermal growth factor for serial cultivation; and 3) inhibition of growth by transforming growth factor β1.

The present invention encompasses a variety of screening assays. In some embodiments, the screening method comprises providing a skin equivalent of the present invention and at least one test compound or product (e.g., a skin care product such as a moisturizer, cosmetic, dye, or fragrance; the products can be in any from, including, but not limited to, creams, lotions, liquids and sprays), applying the product or test compound to skin equivalent, and assaying the effect of the product or test compound on the skin equivalent. A wide variety of assays are used to determine the effect of the product or test compound on the skin equivalent. These assays include, but are not limited to, MTT cytotoxicity assays (Gay, The Living Skin Equivalent as an In Vitro Model for Ranking the Toxic Potential of Dermal Irritants, Toxic. In Vitro (1992)) and ELISA to assay the release of inflammatory modulators (e.g., prostaglandin E2, prostacyclin, and interleukin-1-alpha) and chemoattractants. The assays can be further directed to the toxicity, potency, or efficacy of the compound or product.

Additionally, the effect of the compound or product on growth, barrier function, or tissue strength can be tested.

In particular, the present invention contemplates the use of the skin equivalents for high throughput screening of compounds from combinatorial libraries (e.g., libraries containing greater than $10^4$ compounds). In some embodiments, the cells are used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the skin equivalents are treated with a compound or plurality of compounds (e.g., from a combinatorial library) and assayed for the presence or absence of a second messenger response. In some preferred embodiments, the cells (e.g., NIKS cells) used to create the skin equivalents are transfected with an expression vector encoding a recombinant cell surface receptor, ion-channel, voltage gated channel or some other protein of interest involved in a signaling cascade. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, IP3, cAMP, arachidonic acid release) due to stimulation of membrane receptors and ion channels (e.g., ligand gated ion channels) (Denyer et al., Drug Discov. Today 3:323-32 (1998); Gonzales et al., Drug. Discov. Today 4:431-39 (1999)). Examples of reporter molecules include, but are not limited to, florescence resonance energy transfer systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the cells comprising the skin equivalents are loaded with the indicator prior to exposure to the compound. Responses of the host cells to treatment with the compounds can be detected by methods known in the art, including, but not limited to, fluorescence microscopy, confocal microscopy, flow cytometry, microfluidic devices, FLIPR systems (Schroeder and Neagle, J. Biomol. Screening 1:75-80 (1996)), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The skin equivalents of the present invention are also useful in reporter gene assays. Reporter gene assays involve the use of host cells transfected with vectors encoding a nucleic acid comprising transcriptional control elements of a target gene (i.e., a gene that controls the biological expression and function of a disease target or inflammatory response) spliced to a coding sequence for a reporter gene. Therefore, activation of the target gene results in activation of the reporter gene product. This serves as indicator of response such an inflammatory response. Therefore, in some embodiments, the reporter gene construct comprises the 5' regulatory region (e.g., promoters and/or enhancers) of a gene that is induced due to skin inflammation or irritation or protein that is involved in the synthesis of compounds produced in response to inflammation or irritation (e.g., prostaglandin or prostacyclin) operably linked to a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green, red, yellow, or blue fluorescent protein, is detected through the use of chemiluminescent, calorimetric, or bioluminecent products of specific substrates (e.g., X-gal and luciferin). Comparisons between compounds of known and unknown activities may be conducted as described above.

In other preferred embodiments, the skin equivalents find use for screening the efficacy of drug introduction across the skin or the affect of drugs directed to the skin. In these embodiments, the skin equivalents are treated with the drug delivery system or drug, and the permeation, penetration, or retention or the drug into the skin equivalent is assayed. Methods for assaying drug permeation are provided in Asbill et al., Pharm Res. 17(9): 1092-97 (2000). In some embodiments, the skin equivalents are mounted on top of modified Franz diffusion cells. The skin equivalents are allowed to hydrate for one hour and then pretreated for one hour with propylene glycol. A saturated suspension of the model drug in propylene glycol is then added to the skin equivalent. The skin equivalent can then be sampled at predetermined intervals. The skin equivalents are then analyzed by HPLC to determine the concentration of the drug in the sample. Log P values for the drugs can be determined using the ACD program (Advanced Chemistry Inc., Ontario, Canada). These methods may be adapted to study the delivery of drugs via transdermal patches or other delivery modes.

In still further preferred embodiments, the seeded dermal equivalents, which have not yet undergone differentiation, find use in assays for compounds that inhibit, accelerate, or otherwise effect differentiation of the seeded keratinocytes.

2. Substrates For Culturing Tumors and Pathological Agents

It is contemplated that skin equivalents of the present invention are also useful for the culture and study of tumors that occur naturally in the skin as well as for the culture and study of pathogens that affect the skin. Accordingly, in some embodiments, it is contemplated that the skin equivalents of the present invention are seeded with malignant cells. By way of non-limiting example, the skin equivalents can be seeded with malignant SCC13y cells as described in U.S. Pat. No. 5,989,837, which is incorporated herein by reference, to provide a model of human squamous cell carcinoma. These seeded skin equivalents can then be used to screen compounds or other treatment strategies (e.g., radiation or tomotherapy) for efficacy against the tumor in its natural environment. Thus, some embodiments of the present invention provide methods comprising providing a skin equivalent comprising malignant cells or a tumor and at least one test compound, treating the skin equivalent with the compound, and assaying the effect of the treatment on the malignant cells or tumors. In other embodiments of the present invention, methods are provided that comprise providing a skin equivalent comprising malignant cells or a tumor and at least one test therapy (e.g., radiation or phototherapy) treating the skin equivalent with the therapy, and assaying the effect of the therapy on the malignant cells or tumors.

In other embodiments, the skin equivalents are used to culture and study skin pathogens. By way of non-limiting example, the skin equivalents are infected with human papilloma virus (HPV) such as HPV18. Methods for preparing skin equivalents infected with HPV are described in U.S. Pat. No. 5,994,115, which is incorporated herein by reference. Thus, some embodiments of the present invention provide methods comprising providing a skin equivalent infected with a pathogen of interest and at least one test compound or treatment and treating the skin equivalent with the test compound or treatment. In some preferred embodiments, the methods further comprise assaying the effect the test compound or treatment on the pathogen. Such assays may be conducted by assaying the presence, absence, or quantity of the pathogen in the skin substitute following treatment. For example, an ELISA may be performed to detect or quantify the pathogen. In some particularly preferred embodiments, the pathogen is viral pathogen such as HPV.

3. Wound Closure and Burn Treatment

The skin equivalents of the present invention find use in wound closure and burn treatment applications. The use of autografts and allografts for the treatment of burns and wound closure is described in Myers et al., A. J. Surg. 170(1):75-83 (1995) and U.S. Pat. Nos. 5,693,332; 5,658,331; and 6,039,760, each of which is incorporated herein by reference. In some embodiments, the skin equivalents may be used in conjunction with dermal replacements such as DERMAGRAFT. In other embodiments, the skin equivalents are produced using both a standard source of keratinocytes (e.g., NIKS cells) and keratinocytes from the patient that will receive the graft. Therefore, the skin equivalent contains keratinocytes from two different sources. In still further embodiments, the skin equivalent contains keratinocytes from a human tissue isolate. Accordingly, the present invention provides methods for wound closure, including wounds caused by burns, comprising providing a skin equivalent according to the present invention and a patient suffering from a wound and treating the patient with the skin equivalent under conditions such that the wound is closed.

4. Gene Therapy

In still further embodiments, the skin equivalent is engineered to provide a therapeutic agent to a subject. The present invention is not limited to the delivery of any particular therapeutic agent. Indeed, it is contemplated that a variety of therapeutic agents may be delivered to the subject, including, but not limited to, enzymes, peptides, peptide hormones, other proteins, ribosomal RNA, ribozymes, and antisense RNA. These therapeutic agents may be delivered for a variety of purposes, including but not limited to the purpose of correcting genetic defects. In some particular preferred embodiments, the therapeutic agent is delivered for the purpose of detoxifying a patient with an inherited inborn error of metabolism (e.g., aninoacidopathesis) in which the graft serves as wild-type tissue. It is contemplated that delivery of the therapeutic agent corrects the defect. In some embodiments, the keratinocytes used to form the skin equivalent are transfected with a DNA construct encoding a therapeutic agent (e.g., insulin, clotting factor IX, erythropoietin, etc) and the skin equivalent is grafted onto the subject. The therapeutic agent is then delivered to the patient's bloodstream or other tissues from the graft. In preferred embodiments, the nucleic acid encoding the therapeutic agent is operably linked to a suitable promoter. The present invention is not limited to the use of any particular promoter. Indeed, the use of a variety of promoters is contemplated, including, but not limited to, inducible, constitutive, tissue-specific, and keratinocyte-specific promoters. In some embodiments, the nucleic acid encoding the therapeutic agent is introduced directly into the keratinocytes (i.e., by calcium phosphate co-precipitation or via liposome transfection). In other preferred embodiments, the nucleic acid encoding the therapeutic agent is provided as a vector and the vector is introduced into the keratinocytes by methods known in the art. In some embodiments, the vector is an episomal vector such as a plasmid. In other embodiments, the vector integrates into the genome of the keratinocytes. Examples of integrating vectors include, but are not limited to, retroviral vectors, adeno-associated virus vectors, and transposon vectors.

D. Use of Methods of Production of Other Products Substantially Free of Feeder Layer Cells The present invention contemplates the production of a variety of cells, cell lines, or cell-derived products that are substantially free of residual feeder layer cells. In preferred embodiments, cells or cell lines grown on 3T3 feeder layers screened with the mouse DNA assay and proliferation assay will result in cultured cells or cell lines that are substantially free of feeder layer cells. In some preferred embodiments of the present invention, stem cells substantially free of feeder layers are harvested. The present invention is not limited to a particular stem cell type. Specific stem cells from any organism may be utilized. In some preferred embodiments, the stem cell type may be adult stem cells (e.g., somatic stem cells). In other preferred embodiments, the stem cell type may be embryonic stem cells (e.g., totipotent stem cells).

In some embodiments, the method of stem cell isolation described in U.S. Pat. No. 5,843,780 (herein incorporated by reference) is utilized. In such embodiments, the medium for isolation of embryonic stem cells is "ES medium." ES medium consists of 80% Dulbecco's modified Eagle's medium (DMEM; no pyruvate, high glucose formulation, Gibco ERL), with 20% fetal bovine serum (FBS; Hyclone), 0.1 mM β-mercaptoethanol (Sigma), 1% non-essential amino acid stock (Gibco BRL). Preferably, fetal bovine serum batches are compared by testing clonal plating efficiency of a low passage mouse ES cell line ($ES_{jt3}$), a cell line developed just for the purpose of this test. FBS batches must be compared because it has been found that batches vary dramatically in their ability to support embryonic cell growth, but any other method of assaying the competence of FBS batches for support of embryonic cells will work as an alternative.

Primate ES cells are isolated on a confluent layer of murine embryonic fibroblast in the presence of ES cell medium. Embryonic fibroblasts are preferably obtained from 12 day old fetuses from outbred CF1 mice (SASCO), but other strains may be used as an alternative. Tissue culture dishes are preferably treated with 0.1% gelatin (type I; Sigma).

For rhesus monkey embryos, adult female rhesus monkeys (greater than four years old) demonstrating normal ovarian cycles are observed daily for evidence of menstrual bleeding (day 1 of cycle=the day of onset of menses). Blood samples are drawn daily during the follicular phase starting from day 8 of the menstrual cycle, and serum concentrations of luteinizing hormone are determined by radioimmunoassay. The female is paired with a male rhesus monkey of proven fertility from day 9 of the menstrual cycle until 48 hours after the luteinizing hormone surge; ovulation is taken as the day following the luteinizing hormone surge. Expanded blastocysts are collected by non-surgical uterine flushing at six days after ovulation. This procedure routinely results in the recovery of an average 0.4 to 0.6 viable embryos per rhesus monkey per month, Seshagiri et al. Am J Primatol 29: 81-91, 1993.

For marmoset embryos, adult female marmosets (greater than two years of age) demonstrating regular ovarian cycles are maintained in family groups, with a fertile male and up to five progeny. Ovarian cycles are controlled by intramuscular injection of 0.75 g of the prostaglandin PGF2α analog cloprostenol (Estrumate, Mobay Corp, Shawnee, Kans.) during the middle to late luteal phase. Blood samples are drawn on day 0 (immediately before cloprostenol injection), and on days 3, 7, 9, 11, and 13. Plasma progesterone concentrations are determined by ELISA. The day of ovulation is taken as the day preceding a plasma progesterone concentration of 10 ng/ml or more. At eight days after ovulation, expanded blastocysts are recovered by a non-surgical uterine flush procedure, Thomson et al. "Non-surgical uterine stage preimplantation embryo collection from the common marmoset," J Med Primatol, 23: 333-336 (1994). This procedure results in the average production of 1.0 viable embryos per marmoset per month.

The zona pellucida is removed from blastocysts by brief exposure to pronase (Sigma). For immunosurgery, blastocysts are exposed to a 1:50 dilution of rabbit anti-marmoset spleen cell antiserum (for marmoset blastocysts) or a 1:50 dilution of rabbit anti-rhesus monkey (for rhesus monkey blastocysts) in DMEM for 30 minutes, then washed for 5 minutes three times in DMEM, then exposed to a 1:5 dilution of Guinea pig complement (Gibco) for 3 minutes.

After two further washes in DMEM, lysed trophectoderm cells are removed from the intact inner cell mass (ICM) by gentle pipetting, and the ICM plated on mouse inactivated (3000 rads gamma irradiation) embryonic fibroblasts.

After 7-21 days, ICM-derived masses are removed from endoderm outgrowths with a micropipette with direct observation under a stereo microscope, exposed to 0.05% Trypsin-EDTA (Gibco) supplemented with 1% chicken serum for 3-5 minutes and gently dissociated by gentle pipetting through a flame polished micropipette.

Dissociated cells are replated on embryonic feeder layers in fresh ES medium, and observed for colony formation. Colonies demonstrating ES-like morphology are individually selected, and split again as described above. The ES-like morphology is defined as compact colonies having a high nucleus to cytoplasm ratio and prominent nucleoli. Resulting ES cells are then routinely split by brief trypsinization or exposure to Dulbecco's Phosphate Buffered Saline (without calcium or magnesium and with 2 mM EDTA) every 1-2 weeks as the cultures become dense. Early passage cells are also frozen and stored in liquid nitrogen.

Cell lines may be karyotyped with a standard G-banding technique (such as by the Cytogenetics Laboratory of the University of Wisconsin State Hygiene Laboratory, which provides routine karyotyping services) and compared to published karyotypes for the primate species.

Isolation of ES cell lines from other primate species would follow a similar procedure, except that the rate of development to blastocyst can vary by a few days between species, and the rate of development of the cultured ICMs will vary between species. For example, six days after ovulation, rhesus monkey embryos are at the expanded blastocyst stage, whereas marmoset embryos don't reach the same stage until 7-8 days after ovulation. The Rhesus ES cell lines were obtained by splitting the ICM-derived cells for the first time at 7-16 days after immunosurgery; whereas the marmoset ES cells were derived with the initial split at 7-10 days after immunosurgery. Because other primates also vary in their developmental rate, the timing of embryo collection, and the timing of the initial ICM split will vary between primate species, but the same techniques and culture conditions will allow ES cell isolation.

Because ethical considerations in the U.S. do not allow the recovery of human in vivo fertilized preimplantation embryos from the uterus, human ES cells that are derived from preimplantation embryos will be derived from in vitro fertilized (IVF) embryos. Experiments on unused (spare) human IVF-produced embryos are allowed in many countries, such as Singapore and the United Kingdom, if the embryos are less than 14 days old. Only high quality embryos are suitable for ES isolation. Present defined culture conditions for culturing the one cell human embryo to the expanded blastocyst are suboptimal but practicable, Bongso et al., Hum Reprod 4: 706-713, 1989. Co-culturing of human embryos with human oviductal cells results in the production of high blastocyst quality. IVF-derived expanded human blastocysts grown in cellular co-culture, or in improved defined medium, will allow the isolation of human ES cells with the same procedures described above for nonhuman primates.

In other preferred embodiments the present invention contemplates producing a variety of other cells or cell lines substantially free of feeder layer cells including wet stratified barrier epithelia (e.g., surface epithelial cells, cells of the urinary epithelium); epithelial cells specialized for exocrine secretion (e.g., salivary gland cells, mammary gland cells, apocrine sweat gland cells, mucous cells of the stomach lining); cells specialized for secretion of hormones (e.g., secreting cells of the pituitary gland, secreting cells of the gut and respiratory tract, secreting cells of the thyroid gland, secreting cells of the adrenal gland, secreting cells of the gonads); epithelial absorptive cells in gut, exocrine glands, and urogential tract (e.g., brush border cells of the intestine, striated duct cells of the exocrine glands, nonciliated cells of the ductulus efferens); cells specialized for metabolism and storage (e.g., hepatocytes, fat cells); epithelial cells serving primarily a barrier function, lining the lung, gut, exocrine glands, and urogenital tract (e.g., type 1 pneumocytes, pancreatic duct cells, parietal cells of kidney glomerulus); epithelial cells lining closed internal body cavities (e.g., vascular endothelial cells of blood vessels and lymphatics, synovial cells, cells lining endolymphatic space of ear, corneal "endothelial" cells); ciliated cells with propulsive function (e.g., respiratory tract cells, oviduct cells, ependymal cell lining of brain cavities); cells specialized for secretion of extracellular matrix (e.g., ameloblast cells, fibroblasts, pericytes of blood capillaries, chondrocytes, osteoblasts); contractile cells (e.g., skeletal muscle cells, heart muscle cells, smooth muscle cells, myoepithelial cells); cells of blood and immune system (e.g., red blood cells, macrophages, neutrophils, T lymphocytes, B lymphocytes); sensory transducers (e.g., photoreceptors, inner hair cell of organ of Corti, type II taste bud cells); autonomic neurons (e.g., cholinergic cells, adrenergic cells, peptidergic cells); supporting cells of sense organs and of peripheral neurons (e.g., inner pillar cells, Hensen cells, Schwann cells, enteric glial cells); neurons and glial cells of central nervous system (e.g., neuronal cells in general, astrocytes, oligodendrocytes); lens cells (e.g., anterior lens epithelial cell, lens fiber cell); pigment cells (e.g., melanocytes, retinal pigmented epithelial cells); germ cells (e.g., oogonium cells, oocytes, spermatocytes, spermatogonium); nurse cells (e.g., ovarian follicle cells, Sertoli cells, thymus epithelial cell).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); C (degrees Centigrade); U (units), mU (milliunits); min. (minutes); sec. (seconds); % (percent); kb (kilobase); bp (base pair); PCR (polymerase chain reaction); BSA (bovine serum albumin).

EXAMPLE 1

Detection of Mouse-Specific DNA Using Mouse Primers ST051 and ST052

This example describes the detection of mouse-specific DNA using the mouse primers ST051 and ST052. Genomic DNA was isolated from mouse (3T3) and normal human dermal fibroblast (NHDF) cells for use as PCR templates. PCR primers ST051 (5'-GAATTCACTATGAAAGTCA-GATTAGATC-3'; SEQ ID NO:1) and ST052 (5'-GAATTC-CATAACCATTACAGTTGGCCAACC-3'; SEQ ID NO:2) were designed to amplify a 285 base pair (bp) product specific to mouse genomic DNA (MacGregor, H. C. and Varley, J. M. (1988). "Working with Animal Chromosomes," 2$^{nd}$ ed., Wiley, N.Y.).

PCR reactions contained mouse cell (3T3) genomic DNA (123 ng/reaction) or human cell (NHDF) genomic DNA (100 ng/reaction). Following denaturation at 95° C. for 4 minutes, samples were subjected to the following for 35 cycles: Denaturation at 94° C. for 1 minute, Annealing at 50° C. for 1 minute, Extension at 72° C. for 2 minutes. A final extension at 72° C. for 7 minutes was followed by a 4° C. hold.

The 285 bp product amplified well when mouse (3T3) genomic DNA was tested with mouse-specific DNA primers ST051 and ST052. At the same time no PCR product was detected in human cell (NHDF) genomic DNA sample when assayed with mouse-specific DNA primers.

EXAMPLE 2

Detection of Human-Specific DNA Using Control PCR Primers ST047 and ST035

This example describes the use of a second set of primers (ST047 (5'-GCCCGGCCCCTCTTGTCCCC-3'; SEQ ID NO:3) and ST035 (5'-GAGCCGGGGTCATCCGGTG-3'; SEQ ID NO:4) to amplify a 500 bp specific product from human genomic DNA. This example also describes the systematic evaluation and identification of optimal primer-template annealing conditions for both mouse and control PCR primer sets.

PCR reactions contained either human genomic DNA (Promega, Madison, Wis.) (0.5 µg/reaction), mouse cell (3T3) genomic DNA (250 µg/reaction), or human genomic DNA (Promega) (0.5 µg/reaction)+mouse cell (3T3) genomic DNA spike (250 µg/reaction). Following denaturation at 95° C. for 5 minutes, samples were subjected to the following for 30 cycles: Denaturation at 94° C. for 1 minute, Annealing conditions ranging 50° C.-70° C. for 1 minute, Extension at 72° C. for 2 minutes. A final extension at 72° C. for 7 minutes was followed by a 4° C. hold.

Primers ST047 and ST035 serve as a control PCR primer set used to verify the integrity of template genomic DNA for its ability to be PCR amplified. These control primers produce different size PCR products that correspond to each of the different species of genomic DNA tested. Expected PCR primer control product sizes are as follows: 400 bp (mouse), 500 bp & 300 bp (human).

Primers ST047 and ST035 specifically amplified the expected 500 bp and 300 bp PCR product from human genomic DNA template. PCR primers ST051 and ST052 specifically amplified a 285 bp PCR product from a mouse genomic DNA template. Band intensity remained relatively constant with or without the addition of a (0.5 µg) human genomic DNA spike. Optimal annealing temperatures of 57.3° C. and 68.6° C. were identified for the respective mouse-specific and human PCR primer sets.

EXAMPLE 3

PCR Using Skin Culture Biopsy Samples

This example describes the isolation of genomic DNA from STRATAGRAFT (Stratatech Corp., Madison, Wis.) biopsy samples for evaluation as a genomic DNA template source in the PCR assays described in Examples 1 and 2. Total genomic DNA was isolated from pooled (MacGreagor, H. C. (1988) In: Working with Animal Chromosomes, 2$^{nd}$ Ed., Wiley, N.Y.) biopsy punches from the same STRATAGRAFT and used as a template for PCR amplification using control primers ST047 and ST035.

Genomic DNA templates for PCR reactions were one of the following: mouse cell (3T3) genomic DNA; human cell (NIKS) genomic DNA; human genomic DNA (Promega) (0.5 µg/reaction); human genomic DNA (Promega) (0.5 µg/reaction)+mouse cell (3T3) genomic DNA spike (range 10-250 pg/reaction); STRATAGRAFT genomic DNA (0.5 µg/reaction).

Following denaturation at 95° C. for 5 minutes, samples were subjected to the following for 30 cycles: Denaturation at 94° C. for 1 minute, Annealing at 57.3° C. for 1 minute, Extension at 72° C. for 2 minutes. A final extension at 72° C. for 7 minutes was followed by a 4° C. hold.

The amount and integrity of genomic DNA isolated from STRATAGRAFT biopsy samples was found to be sufficient for analysis in a PCR assay. Control primers demonstrated the ability to amplify human genomic sequences from STRATAGRAFT biopsy genomic DNA. These results confirm the use of these control primers as reliable internal PCR control to validate amplification of genomic DNA samples.

EXAMPLE 4

Evaluation of Mouse-Specific DNA Detection Limits

This example describes the evaluation of mouse-specific DNA detection limits of this assay in a PCR reaction containing 0.5 µg of total human genomic DNA.

Genomic DNA Templates for PCR reactions were one of the following: human genomic DNA (Promega) (0.5 µg/reaction); mouse cell (3T3) genomic DNA (123 ng/reaction); human genomic DNA (Promega) (0.5 µg/reaction)+mouse cell (3T3) genomic DNA spike (range 25-500 pg/reaction). Mouse-specific PCR primers ST051 and ST052 were used.

Following denaturation at 95° C. for 4 minutes, samples were subjected to the following for 30 cycles: Denaturation at 94° C. for 1 minute, Annealing at 55° C. for 1 minute, Extension at 72° C. for 2 minutes. A final extension at 72° C. for 10 minutes was followed by a 4° C. hold.

The results indicated that the mouse DNA detection limit is 250 pg of mouse genomic DNA in a PCR reaction containing 0.5 µg total human genomic DNA. Modification of the specific PCR assay conditions (e.g., number of cycles) may be utilized to improve the specified mouse DNA limit of detection.

EXAMPLE 5

Assay Variability and Reproducibility

This example describes an investigation of assay variability and reproducibility on the following:
1) Multiple biopsy DNA preparations from the same STRATAGRAFT sample.
2) Multiple STRATAGRAFT samples from the same production batch.
3) Multiple samples from the same batch of STRATAGRAFT by different production operators.

Genomic DNA templates for PCR reactions were one of the following: STRATAGRAFT genomic DNA (0.5 µg/reaction); human genomic DNA (Promega) (0.5 µg/reaction); human genomic DNA (Promega) (0.5 µg/reaction)+mouse cell (3T3) genomic DNA spike (100 or 250 pg/reaction). Mouse-specific PCR primers ST051 and ST052 were used, in addition, control primers ST047 and ST035 were also used in parallel reactions.

Following denaturation at 94° C. for 5 minutes, samples were subjected to the following for 30 cycles: Denaturation at 94° C. for 1 minute, Annealing at 61° C. for 1 minute, Extension at 72° C. for 2 minutes. A final extension at 72° C. for 7 minutes was followed by a 4° C. hold.

Only slight variability in the amount of the PCR product was detected as a result of multiple STRATAGRAFF DNA isolations, STRATAGRAFT preparations or STRATAGRAFT production operators. The observed PCR product variation is not significant and is expected as a normal result of a semi-quantitative PCR assay.

EXAMPLE 6

Titration of Mouse Cells

This example describes the verification of the detection limits that were previously calculated using mouse DNA equivalents by adding a known number of mouse 3T3 cells to a predetermined number of NHDF cells. A decreasing percentage of mouse cells were titrated into a constant number of NHDF cells. Genomic DNA was isolated from these cell populations for subsequent PCR analysis. The intensities of the PCR products from the mixed-cell populations were compared to those obtained by mixing known amounts of mouse genomic DNA with human genomic DNA.

A semi-quantitative estimate of mouse cell-specific DNA is based on $3.5 \times 10^{-12}$ g of mouse DNA per haploid chromosome set (MacGregor and Varley, 1988). Therefore, 250 pg of mouse genomic DNA equates to 35.7 mouse cell DNA equivalents. A human genomic DNA template sample of 0.5 µg is equivalent to 90,000 human cells.

Genomic DNA templates for PCR reactions were one of the following: mixed cell (NHDF/3T3) population genomic DNA (0.5 µg/reaction); human cell (NHDF) genomic DNA (0.5 µg/reaction); mouse cell (3T3) genomic DNA (0.5 µg/reaction); human genomic DNA (Promega) (0.5 µg/reaction); human genomic DNA (Promega) (0.5 µg/reaction)+mouse cell (3T3) genomic DNA (3.1-250 µg/reaction). Mouse-specific PCR primers ST051 and ST052 were used, in addition, control primers ST047 and ST035 were also used in parallel reactions.

Following denaturation at 95° C. for 5 minutes, samples were subjected to the following for 30 cycles: Denaturation at 94° C. for 1 minute, Annealing at 61° C. for 1 minute, Extension at 72° C. for 2 minutes. A final extension at 72° C. for 7 minutes was followed by a 4° C. hold.

The intensity of the PCR products obtained using DNA isolated from mixed-cell populations were comparable to the intensity obtained from mouse DNA equivalent spiked samples as presented in Tables 2 and 3.

These results demonstrated the ability of the PCR assay able to detect less than four mouse cells in a background of approximately 90,000 human cells. Thus, this assay will detect low-level residual mouse cells in the presence of human cells.

TABLE 2

Detection Results Using Spiked Mouse Cells

| Mouse Cell Number Spiked into 90,000 Human Cells | PCR Result |
|---|---|
| 265 cells | Detected |
| 132 cells | Detected |
| 66.1 cells | Detected |
| 13.2 cells | Detected |
| 6.6 cells | Detected |
| 3.3 cells | Detected |
| 0 (No Mouse Cells) | Non-Detected |

TABLE 3

Detection Results Using Spiked Isolated Mouse DNA

| Amount of Mouse Genomic DNA spiked into 0.5 µg Human Genomic DNA | Approximate Cell Equivalents | PCR Result |
|---|---|---|
| 250 pg | 36 | Detected |
| 125 pg | 18 | Detected |
| 62.5 pg | 9 | Detected |
| 12.5 pg | 2 | Detected |
| 6.25 pg | 1 | Non-Detected |
| 3.125 pg | 0.5 | Non-Detected |
| 0 (No Mouse DNA) | 0 | Non-Detected |

EXAMPLE 7

Cross-Reactivity of Mouse-Specific Primers

This example demonstrates that no non-mouse DNA was detected with mouse-specific primers in non-mouse samples.

Genomic DNA templates for PCR reactions were one of the following: human genomic DNA (Promega) (0.5 µg/reaction); human genomic DNA (Clontech) (0.5 µg/reaction); rat genomic DNA (Clontech) (0.5 µg/reaction); rat genomic DNA (Stratatech) (0.5 µg/reaction); mouse genomic DNA (Clontech) (0.5 µg/reaction); mouse cell (3T3) genomic DNA (0.5 µg/reaction); mouse cell (3T3) genomic DNA (250 pg/reaction); mouse genomic DNA (Clontech) (250 pg/reaction); STRATAGRAFT A genomic DNA (0.5 µg/reaction); STRATAGRAFT B genomic DNA (0.5 µg/reaction); negative Control (No DNA).

Following denaturation at 95° C. for 5 minutes, samples were subjected to the following for 30 cycles: Denaturation at 94° C. for 1 minute, Annealing at 61° C. for 1 minute, Extension at 72° C. for 2 minutes. A final extension at 72° C. for 7 minutes was followed by a 4° C. hold.

Mouse-specific primers ST051 and ST052 demonstrated the absence of cross-reactivity or non-specific amplification of rat and human genomic DNA sequences. These primers are therefore specific to mouse genomic DNA sequences.

EXAMPLE 8

Determination of the Optimal Number of Mitomycin-C-Treated 3T3 Fibroblasts per $cm^2$ for the Detection of Proliferating 3T3 Cells This example describes the experiments used to determine the optimal number of mitomycin-C-treated 3T3 fibroblasts per $cm^2$. During the production of STRATAGRAFT approximately $7.5 \times 10^6$ mitomycin-C-treated replication-inactivated 3T3 cells are used during NIKS initiation and approximately $25 \times 10^6$ mitomycin-C-treated replication-inactivated 3T3 cells are used during NIKS expansion. The mitomycin-C-treated replication-inactivated 3T3 feeder layers are plated at a cell density that ranges between 22,700 cells/$cm^2$ as per BR14 and 27,300 cells/$cm^2$ as per BR13. To determine the optimal number of mitomycin-C-treated 3T3 fibroblasts per $cm^2$ for the detection of proliferating 3T3 cells, four different cell densities of 3,130 cells/$cm^2$, 7,810 cells/$cm^2$, 15,630 cells/$cm^2$ and 31,250 cells/$cm^2$ were examined using 96-well plates. These densities correspond to 1000, 2500, 5000, and 10,000 mitomycin-C-treated 3T3 fibroblasts per well (0.32 $cm^2$/well).

To determine which cell density would best support the proliferation and subsequent detection of any 3T3 mouse fibroblast capable of replication, untreated, proliferating 3T3 cells (cells never treated with mitomycin-C) were combined with mitomycin-C-treated 3T3 fibroblasts in specific combinations as diagrammed in FIG. 1. Five 96-well plates, a total of 153.6 $cm^2$, were utilized per cell density tested, with each of these 96-well plates containing 25 untreated, proliferating 3T3 cells diluted to the extent that each well had an approximately one-in-four chance of containing a single 3T3 mouse fibroblast capable of replication.

A control for both the appropriate dilution of replication-competent 3T3 fibroblasts and the level of 3T3 proliferation in the absence of mitomycin-C-treated 3T3 fibroblasts was also included in this assay. Five 96-well plates containing only 25 untreated, proliferating 3T3 cells were used for this purpose. The proliferating 3T3 cells were diluted to the extent that each well of the control plates had an approximately one-in-four chance of chance of containing a single 3T3 mouse fibroblast capable of replication.

Cultures of proliferating, replication-competent 3T3M1 cells, a thioguanine-resistant variant of the Swiss mouse fibroblast 3T3 line, were maintained as previously described (Allen Hoffman, B. L. and Rheinwald, J. G. (1994) 81 Proc. Natl. Acad. Sci. USA 7802-7806) in culture medium composed of Dulbecco's modified Eagle's medium supplemented with 10% fetal calf serum. Cryopreserved mitomycin-C-treated 3T3 cells were prepared according to Stratatech protocol BR10. In all experiments, exhausted medium was removed and replaced with 200 μl fresh medium per well each week during incubation. Microscopic examination to verify an even cell distribution was completed after the first week of incubation. Rigorous examination for evidence of bacterial contamination was also completed throughout the course of culturing. The limited surface area for cellular growth in the 96-well plate format (0.32 $cm^2$/well) facilitated orientation during microscopic examination and restricted proliferative 3T3 migration.

After three weeks of incubation, samples were fixed for 30 minutes in 10% formalin and stained overnight with a 0.2% methylene blue solution. Methylene blue stains basophilic cellular compounds, primarily nucleic acids, in both replication-competent and replication-incompetent 3T3 cells (Scragg, M. A. and Ferreira, L. R. (1991) 198:1 Anal. Biochem. 80-85). Stained plates were washed extensively with water to remove excess methylene blue and allowed to air-dry.

Each methylene blue-stained well was examined both visually and microscopically for evidence of 3T3 proliferation. Staining permits rapid identification of cells and aids microscopic examination of cellular morphology. The cellular morphology of an actively proliferating 3T3 cell is quite different from that of a mitomycin-C-treated replication-inactivated 3T3 cell facilitating clear distinction between these two states. Proliferating 3T3 cells are colony-associated and are small and fusiform in appearance. Conversely, mitomycin-C-treated replication-inactivated 3T3 cells are large and flat in appearance. Based on microscopic identification and classification by morphological appearance, each well was individually recorded as either positive or negative for 3T3 proliferation.

Two replicates of the assay were completed comparing 3T3 proliferation detection within a background of four different mitomycin-C-treated 3T3 fibroblast densities (1000, 2500, 5000, and 10,000 cells per well) to 3T3 proliferation detection in a control background of 0 mitomycin-C-treated 3T3 fibroblasts per well (0.32 $cm^2$/well). As designed, five 96-well plates were utilized per cell density tested, with each of these 96-well plates containing 25 untreated, proliferating 3T3 cells diluted to the extent that each well had an approximately one-in-four chance of containing a single 3T3 mouse fibroblast capable of replication.

To verify that the experimental procedure resulted in an even cellular distribution, the number of proliferating 3T3 cells detected was initially analyzed on a per plate basis. The average number of positive wells per 96-well plate was determined for each tested background level of mitomycin-C-treated 3T3 cells per well (Table 4). The average number of positive wells per plate varied with cell density, however the standard deviation values for each set of plates examined were remarkably consistent. This consistency indicated that the procedures resulted in a relatively even distribution of replication-competent, proliferative 3T3 fibroblasts that was not affected by cell density variables.

TABLE 4

Average Number of Wells Positive for 3T3 Proliferation per 96-well Plate for Each Condition Tested

| Number of Mitomycin-C-Treated 3T3 Cells per Well (0.32 $cm^2$) | Replicate 1 | | Replicate 2 | |
| --- | --- | --- | --- | --- |
| | Average | St. Dev. | Average | St. Dev. |
| 0 Cells/Well (0 cells/$cm^2$) | 11.4 | 3.3 | 13.8 | 4.4 |
| 1,000 Cells/Well (3,130 cells/$cm^2$) | 17.8 | 3.6 | 21 | 4.1 |
| 2,500 Cells/Well (7,810 cells/$cm^2$) | 20 | 4.3 | 23.8 | 3.3 |

TABLE 4-continued

Average Number of Wells Positive for 3T3 Proliferation
per 96-well Plate for Each Condition Tested

| Number of Mitomycin-C- Treated 3T3 Cells per Well (0.32 cm$^2$) | Replicate 1 | | Replicate 2 | |
|---|---|---|---|---|
| | Average | St. Dev. | Average | St. Dev. |
| 5,000 Cells/Well (15,630 cells/cm$^2$) | 19 | 3.2 | 24.2 | 5.2 |
| 10,000 Cells/Well (31,250 cells/cm$^2$) | 15.2 | 3.6 | 20.2 | 2.9 |

Figure 2:
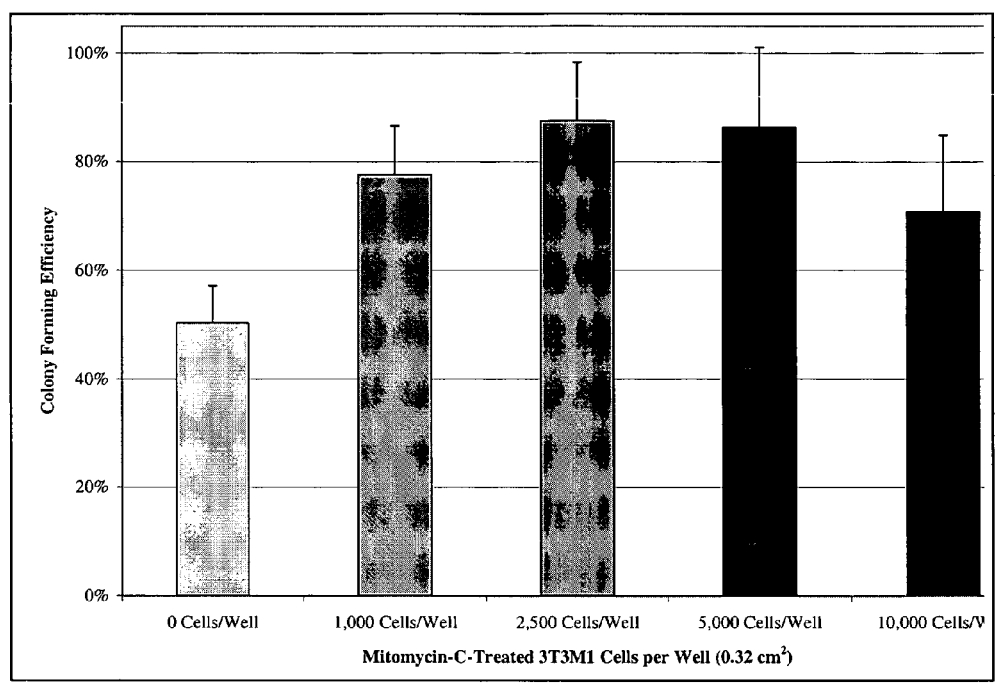
FIG. 2 depicts comparison of conditions tested to determine optimal cell density for the detection of proliferating 3T3 fibroblasts.

The data from Table 4 were analyzed to compare the colony forming efficiency (CFE) of proliferative 3T3 cells plated at each mitomycin-C-treated 3T3 cell density condition (Table 5). The comparison of colony forming efficiencies at each background level tested is depicted in FIG. 2. The cell densities of 2,500 and 5,000 mitomycin-C-treated 3T3 fibroblasts per well (7,810 and 15,630 cells/cm$^2$) appear to support the proliferation and subsequent detection of 3T3 mouse fibroblasts capable of replication equally well and better than the three other cell densities tested.

TABLE 5

Comparison of Colony Forming Efficiency Values for
Each Condition Tested. Comparison of the number of
wells positive for 3T3 proliferation to the theoretical number
of proliferative 3T3 cells added to each condition tested.

| Number of Mitomycin-C- Treated 3T3 Cells per Well (0.32 cm$^2$) | Replicate 1 | | | Replicate 2 | | |
|---|---|---|---|---|---|---|
| | Positive Wells | Total Possible | CFE | Positive Wells | Total Possible | CFE |
| 0 Cells/Well (0 cells/cm$^2$) | 57 | 125 | 46% | 69 | 125 | 55% |
| 1,000 Cells/Well (3,130 cells/cm$^2$) | 89 | 125 | 71% | 105 | 125 | 84% |
| 2,500 Cells/Well (7,810 cells/cm$^2$) | 100 | 125 | 80% | 119 | 125 | 95% |
| 5,000 Cells/Well (15,630 cells/cm$^2$) | 76 | 100 | 76% | 121 | 125 | 97% |
| 10,000 Cells/Well (31,250 cells/cm$^2$) | 76 | 125 | 61% | 101 | 125 | 81% |

| | Average CFE | St. Dev. |
|---|---|---|
| 0 Cells/Well (0 cells/cm$^2$) | 50% | 7% |
| 1,000 Cells/Well (3,130 cells/cm$^2$) | 78% | 9% |
| 2,500 Cells/Well (7,810 cells/cm$^2$) | 88% | 11% |
| 5,000 Cells/Well (15,630 cells/cm$^2$) | 86% | 15% |
| 10,000 Cells/Well (31,250 cells/cm$^2$) | 71% | 14% |

The colony forming efficiency of replication-competent 3T3 fibroblasts was affected by the cell density of mitomycin-C-treated 3T3 cells initially plated. For replication-competent 3T3 cells plated in the absence of mitomycin-C-treated 3T3 cells, a colony forming efficiency of 50% was obtained. A 1.5-fold enhancement of colony forming efficiency resulted from replication-competent 3T3 cells plated in the presence 3,130 mitomycin-C-treated 3T3 cells/cm. For 7,810 and 15,630 mitomycin-C-treated 3T3 cells/cm$^2$, a 1.7-fold enhancement of colony forming efficiency was obtained. A 1.4-fold enhancement of colony forming efficiency was obtained for 3T3 cells plated in the presence 31,250 mitomycin-C-treated 3T3 cells/cm$^2$.

Given these results, the optimal plating density of mitomycin-C-treated 3T3 fibroblasts per cm$^2$ for the detection of proliferating 3T3 cells appears to be between 7,810 and 15,630 cells/cm$^2$. Based on this finding, and the preference to approximate the cell densities used in monolayer culture of NIKS cell for STRATAGRAFT production, the cell density of mitomycin-C-treated 3T3 fibroblasts to be used for the detection of proliferating 3T3 cells was determined to be $1.56 \times 10^4$ cells/cm$^2$.

EXAMPLE 9

Determination of 3T3 Proliferation Detection Sensitivity

Figure 3:
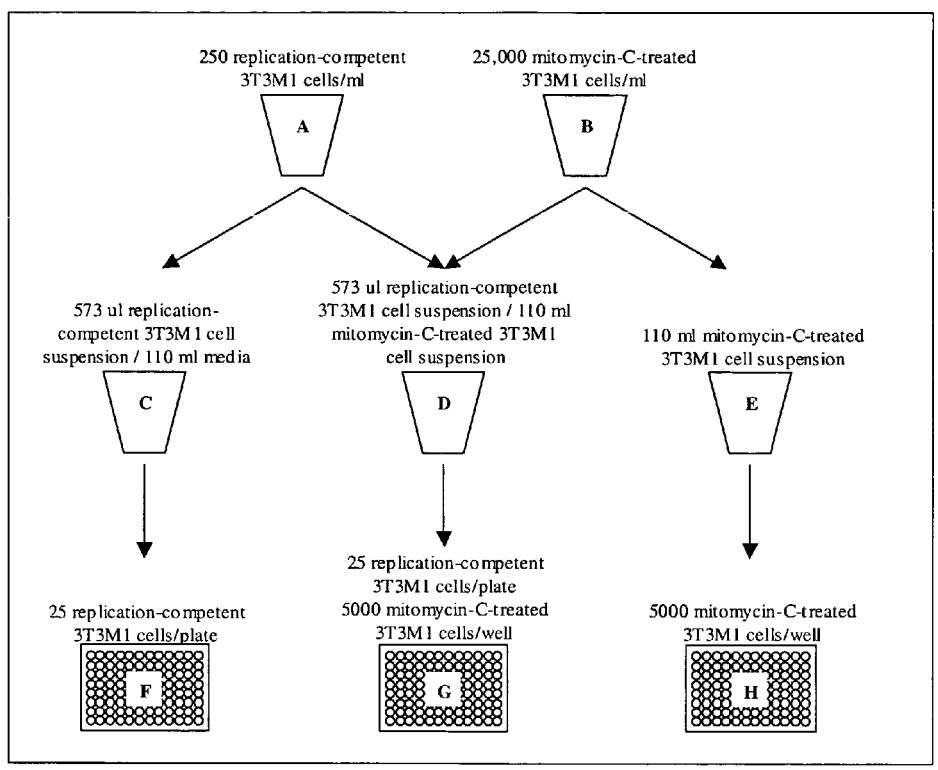
FIG. 3 depicts cellular preparation, dilution, and plating scheme to determine sensitivity of 3T3 proliferation detection. Steps 1 and 2 involve the dilution of cells, steps 3-5 involve the combination of cells, and steps 6-8 involve the plating of cells. In step 1, proliferating, replication-competent 3T3 fibroblasts were harvested, counted, and diluted in 50 ml 3T3 culture medium to a cell density of 250 cells/ml [A]. In step 2, cryopreserved mitomycin-C-treated 3T3 cells were thawed, counted, and diluted in 50 ml 3T3 culture medium to a cell density of 25,000 cells/ml [B]. In step 3, 573 µl of replication-competent 3T3 cell suspension [A] was added to 110 ml of 3T3 culture medium. In step 4, 573 µl of replication-competent 3T3 cell suspension [A] was added to 110 ml of mitomycin-C-treated 3T3 cell suspension [B]. In step 5, 110 ml of mitomycin-C-treated 3T3 cell suspension [B] was reserved for experimental samples. In step 6, 200 µl of replication-competent 3T3 cell suspension [C] was transferred to each well resulting in 25 replication-competent 3T3 cells per plate [F]. In step 7, 200 µl of mitomycin-C-treated 3T3 cell suspension spiked with replication-competent 3T3 fibroblasts [D] was transferred to each well resulting in 5000 mitomycin-C-treated 3T3 cells per well and 25 replication-competent 3T3 cells per plate [G]. In step 8, 200 µl of mitomycin-C-treated 3T3 cell suspension [E] was transferred to each well resulting in 5000 mitomycin-C-treated 3T3 cells per well [H].

This example describes how proliferation detection sensitivity of 3T3 fibroblast cells was determined. To determine the sensitivity of proliferating 3T3 detection, additional experimentation was then completed as described in FIG. 3 employing the optimal cell density previously established. For this evaluation, a specified number of known replication-competent, proliferating 3T3 fibroblasts (never treated with mitomycin-C) were seeded into a specified number of mitomycin-C-treated 3T3 cells per cm2 from several preparations of cryopreserved mitomycin-C-treated 3T3 fibroblasts. Control cultures were included in this experiment to determine the level of replication-competent 3T3 proliferation in the absence of mitomycin-C-treated 3T3 cells. Cultures of mitomycin-C-treated 3T3 cells only were plated to control for possible background levels of 3T3 proliferation arising from incomplete replication-inactivation. Three separate batches of cryopreserved mitomycin-C-treated 3T3 cells were used in this study.

In this experiment, 5000 replication-inactivated 3T3 mouse fibroblasts were plated into each well of five 96-well plates, with each of these 96-well plates containing 25 untreated, proliferating 3T3 cells. The proliferating 3T3 cells were diluted to the extent that each well had an approximately one-in-four chance of containing a single replication-competent 3T3 mouse fibroblast. The cultures were maintained for three weeks to allow replication-competent 3T3 cells to proliferate.

Cultures to control for the level of 3T3 proliferation in the absence of mitomycin-C-treated 3T3 fibroblasts were included in this assay. 96-well plates containing 25 untreated, proliferating 3T3 cells were used for this purpose. The proliferating 3T3 cells were diluted to the extent that each well of the control plates had an approximately one-in-four chance of containing a single replication-competent 3T3 mouse fibroblast.

5000 mitomycin-C-treated 3T3 mouse fibroblasts were plated into each well of five 96-well plates and cultured for three weeks to allow replication-competent 3T3 cells, if present, to proliferate. Evidence of 3T3 proliferation would indicate incomplete mitotic inactivation in the cell population of a given batch.

3T3 fibroblasts were maintained as described in previous experiment. Examination for 3T3 proliferation was completed as described earlier as well.

To determine the sensitivity of 3T3 proliferation detection, samples containing replication-competent 3T3 cells plated in a background of 5,000 mitomycin-C-treated 3T3 cells per well were examined for evidence of 3T3 proliferation. Both sets of control cultures were examined for 3T3 proliferation as well. Table 6 displays the number of wells found to be positive for 3T3 proliferation for each experimental and control plate.

TABLE 6

Number of Positive Wells Detected per Experimental Plate. Wells found to be positive for 3T3 proliferation are recorded for each plate examined. An asterisk denotes a culture that was not plated upon initiation of the experiment.

| Batch Identification | 3T3 Proliferation in the Presence of Mitomycin-C-Treated 3T3 Cells | | | | | Control for 3T3 Proliferation in the Absence of Mitomycin-C-Treated 3T3 Cells | | | | | Control for Proliferation in the Mitomycin-C-Treated 3T3 Cell Population | | | | |
|---|---|---|---|---|---|---|---|---|---|---|---|---|---|---|---|
| | A | B | C | D | E | A | B | C | D | E | A | B | C | D | E |
| FF-121001-SCO | 20 | 18 | 16 | 14 | 21 | 11 | 8 | * | * | * | 0 | 0 | 0 | 0 | 0 |
| FF-031102-06 | 29 | 26 | 18 | 22 | 20 | 12 | 9 | * | * | * | 0 | 2 | 0 | 0 | 0 |
| FF-120301-SCO | 17 | 31 | 23 | 23 | 27 | 15 | 12 | 10 | 11 | 21 | 1 | 0 | 0 | 0 | 0 |

The number of wells found to be positive in the cultures that controlled for background 3T3 proliferation was subtracted from the total number of positive wells found in the experimental plates (Table 7). The resultant colony forming efficiency values for proliferative 3T3 cells plated at the optimal mitomycin-C-treated 3T3 cell density were calculated based on these adjusted values (Table 8).

TABLE 7

Adjusted Number of Positive Wells per Experimental Plate. The number of wells positive for 3T3 proliferation (adjusted for background 3T3 proliferation levels) are recorded for each plate examined.

| Batch Identification Adjusted | 3T3 Proliferation in the Presence of Mitomycin-C-Treated 3T3 Cells | | | Control for 3T3 Proliferation in the Absence of Mitomycin-C-Treated 3T3 Cells Positive Wells |
|---|---|---|---|---|
| | Experimental Positive Wells | Control Positive Wells | Adjusted Positive Wells | |
| FF-121001-SCO | 89 | 0 | 89 | 19 |
| FF-031102-06 | 115 | 2 | 113 | 21 |
| FF-120301-SCO | 121 | 1 | 120 | 69 |

TABLE 8

Comparison of Colony Forming Efficiency Values for Each Batch Tested. Comparison of the number of wells positive for 3T3 proliferation (adjusted for background 3T3 proliferation levels) to the theoretical number of proliferative 3T3 cells added for each batch tested.

| Batch Identification Adjusted | 3T3 Proliferation in the Presence of Mitomycin-C-Treated 3T3 Cells | | | Control for 3T3 Proliferation in the Absence of Mitomycin-C-Treated 3T3 Cells | | |
|---|---|---|---|---|---|---|
| | Positive Wells (adjusted) | Total Possible | CFE | Positive Wells (adjusted) | Total Possible | CFE |
| FF-121001-SCO | 89 | 125 | 71% | 19 | 50 | 38% |
| FF-031102-06 | 113 | 125 | 90% | 21 | 50 | 42% |
| FF-120301-SCO | 120 | 125 | 96% | 69 | 125 | 55% |
| | Average CFE | St. Dev. | | Average CFE | St. Dev. | |
| | 86% | 13% | | 45% | 9% | |

For this examination, the colony forming efficiency for replication-competent 3T3 cells plated in the presence of $1.56 \times 10^4$ mitomycin-C-treated 3T3 cells/cm$^2$ was determined to be 86%±13%. A colony forming efficiency of 45%±9% was calculated for replication-competent 3T3 cells plated in the absence of mitomycin-C-treated 3T3 cells. This nearly 2-fold enhancement in colony forming efficiency when comparing the detection of replication-competent 3T3 cells at a cell density of $1.56 \times 10^4$ mitomycin-C-treated 3T3 fibroblasts/cm$^2$ to that of replication-competent 3T3 cells grown in the absence of mitomycin-C-treated 3T3 fibroblasts is consistent with previous observations (See Table 5).

These numbers take into account the very low level of background 3T3 proliferation detected in two of the three batches tested. 3T3 proliferation indicates that the affected batches were not completely replication-inactivated. These results also reinforce that a very low level of 3T3 proliferation (for example in the case of 1 replication-competent cell out of $2.4 \times 10^6$ cells examined) is detectable using the parameters established for these assays.

To calculate the sensitivity of 3T3 proliferation detection for this set of experiments two values were employed, the colony forming efficiency at the optimal cell density and the total number of cells examined. The resulting colony forming efficiency values were examined and found to be 86%±13%. Therefore, a single replication-competent 3T3 cell has a 73% to 99% chance of establishing a detectable, proliferating 3T3 colony in this specific cellular environment. Examination of $2.4 \times 10^6$ mitomycin-C-treated cells, using the conservative 73% chance of detection per proliferative cell, results in a sensitivity of 3T3 proliferation detection of 1 in $1.75 \times 10^6$ cells.

EXAMPLE 10

Establishing the Parameters for the Test Method: Proliferation Detection in Cryopreserved Mitomycin-C-Treated 3T3 Batches This example describes the experiments used to establish the parameters surrounding the proliferation detection in cryopreserved mitomycin-C-treated 3T3 batches. To clear a batch of mitomycin-C-treated 3T3 cells for use in production, complete mitotic inactivation must be verified. A standard of "No 3T3 Proliferation Detected" (within the understood sensitivity limits of the test) is the only acceptable criteria for this test method. To ensure detection, additional time will be provided extending the original time of culture maintenance from three weeks to a total of five weeks.

The positive control for the test method must incorporate replication-competent 3T3 cells in the appropriate background of mitomycin-C-treated cells. The positive control must also allow for adequate levels of 3T3 proliferation detection between three to five weeks post-plating. Therefore a positive control of a specified number of proliferative 3T3 fibroblasts per culture will be employed in the test method.

The number of cryopreserved mitomycin-C-treated 3T3 fibroblasts required to be tested in the final test method for lot release is based on the chosen format and the sensitivity of 3T3 proliferation detection. Using 225 cm$^2$ tissue culture flasks plated at $1.56 \times 10^4$ cells/cm$^2$ for the test method, the total number of cells per flask examined would be $3.5 \times 10^6$ cells.

It has been established that a single replication-competent 3T3 cell has a 73% to 99% chance of establishing a detectable, proliferating 3T3 colony in this specific cellular environment. Therefore, examination of $7 \times 10^6$ mitomycin-C-treated cells, with at least a 73% chance of detection per proliferative cell, results in a sensitivity of 3T3 proliferation detection of 1 in $5.1 \times 10^6$ cells.

The number of cell DNA equivalents potentially allowable in a dose is no more than $1.45 \times 10^4$ cell DNA equivalents. Therefore, the total of $5.1 \times 10^6$ cells surpasses the number of cell DNA equivalents potentially allowable in a dose by about 350 fold. In addition, testing $7 \times 10^6$ cells provides a 95% confidence interval that there are no replication-competent cells in $1.7 \times 10^6$ cells, which exceeds the number of allowable 3T3 cell DNA equivalents per STRATAGRAFT dose by more than 117 fold.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, biochemistry, or related fields are intended to be within the scope of the following claims.

We claim:

1. A method for forming a skin equivalent for application to a human subject comprising:
   a) providing human product cells, wherein said product cells are near-diploid human keratinocyte (NIKS) cells, providing feeder layer cells, and an agent that prevents cellular replication;
   b) treating said feeder layer cells with said agent that prevents cellular replication to provide replication inactive feeder layer cells;
   c) assaying said replication inactive feeder layer cells for replication, wherein said assay comprises plating said replication inactive feeder layer cells at a density of from about 7,810 to about 15,630 cells/cm$^2$;
   d) cryopreserving said replication inactive feeder layer cells;
   e) thawing said replication inactive feeder layer cells to provide thawed replication inactive feeder layer cells;
   f) culturing said product cells on said thawed replication inactive feeder layer cells;
   g) separating said product cells and said thawed replication inactive feeder layer cells;
   h) assaying a representative portion said product cells for the presence of feeder layer cell DNA;
   i) selecting product cells harvested from a feeder layer for which said representative portion of said product cells contain less than 0.015% feeder cell DNA equivalents within the total cell population; and
   j) forming a skin equivalent from said product cells, and k) assaying said skin equivalent for feeder cell DNA and discarding skin equivalents having more than $1.45 \times 10^4$ murine cell DNA equivalents per NIKS cell dose, wherein a NIKS cell dose is 44.2 cm$^2$ of the finished skin equivalent.

2. The method of claim 1, wherein said product cells are capable of stratifying into squamous epithelia.

3. The method of claim 1, wherein said feeder layer provides growth factors and extracellular matrix molecules.

4. The method of claim 1, wherein the feeder layer is murine fibroblast cells.

5. The method of claim 4, wherein the murine fibroblast cells are 3T3 cells.

6. The method of claim 4, wherein said assaying said product cells for the presence of feeder layer cell DNA is accomplished with a mouse DNA PCR assay.

7. The method of claim 1, wherein said agent is mitomycin-C.

8. The method of claim 1, wherein said separating said product cells and said feeder layer cells is accomplished with EDTA.

9. The method of claim 1, wherein said assaying said feeder layer cells for replication is accomplished with a proliferation assay.

10. The method of claim 9, wherein said feeder layer cells are substantially free of replicating mouse cells.

11. The method of claim 1, wherein said feeder layer cells demonstrating cell replication are discarded.

12. The method of claim 1, wherein said assaying said replication inactive feeder layer cells for replication further comprises assaying about $7 \times 10^6$ replication inactive feeder layer cells.

* * * * *